(12) United States Patent
Chang et al.

(10) Patent No.: US 8,735,150 B2
(45) Date of Patent: May 27, 2014

(54) METHODS FOR DETECTING EMBRYONIC STEM CELLS, INDUCED PLURIPOTENT STEM CELLS, OR CELLS UNDERGOING REPROGRAMMING TO PRODUCE INDUCED PLURIPOTENT STEM CELLS

(75) Inventors: Young-Tae Chang, Singapore (SG); Hyung Ho Ha, Singapore (SG); Nam Young Kang, Singapore (SG); Seong Wook Yun, Singapore (SG); Sung Jin Park, Singapore (SG); Young-Hoon Ahn, Baltimore, MD (US)

(73) Assignees: New York University, New York, NY (US); National University of Singapore, Singapore (SG); Agency for Science, Technology & Research, Singapore (SG)

( * ) Notice: Subject to any disclaimer, the term of this patent is extended or adjusted under 35 U.S.C. 154(b) by 76 days.

(21) Appl. No.: 13/214,782

(22) Filed: Aug. 22, 2011

(65) Prior Publication Data

US 2012/0052505 A1 Mar. 1, 2012

Related U.S. Application Data

(60) Provisional application No. 61/376,665, filed on Aug. 24, 2010.

(51) Int. Cl.
*C12N 5/00* (2006.01)
*G01N 33/567* (2006.01)

(52) U.S. Cl.
USPC ......................................... 435/325; 435/7.21

(58) Field of Classification Search
USPC ................................................ 435/325, 7.21
See application file for complete search history.

(56) References Cited

U.S. PATENT DOCUMENTS

| | | | |
|---|---|---|---|
| 8,026,110 B2 | 9/2011 | Chang et al. |
| 2003/0166002 A1 | 9/2003 | Chang et al. |
| 2004/0122009 A1 | 6/2004 | Chang et al. |
| 2004/0166540 A1 | 8/2004 | Wang et al. |
| 2004/0219669 A1 | 11/2004 | Katsura |
| 2004/0225125 A1 | 11/2004 | Chang |
| 2004/0265252 A1 | 12/2004 | Orlow et al. |
| 2005/0019831 A1 | 1/2005 | Chang |
| 2005/0054006 A1 | 3/2005 | Chang et al. |
| 2005/0227293 A1 | 10/2005 | Chang |
| 2006/0293325 A1 | 12/2006 | Chang et al. |
| 2007/0087435 A1 | 4/2007 | Skorecki et al. |
| 2008/0064037 A1 | 3/2008 | Chang et al. |
| 2008/0124751 A1 | 5/2008 | Chang et al. |
| 2008/0160521 A1 | 7/2008 | Chang et al. |
| 2009/0227467 A1 | 9/2009 | Chang et al. |

FOREIGN PATENT DOCUMENTS

| | | |
|---|---|---|
| WO | 2005/033149 A1 | 4/2005 |
| WO | 2008/115517 A2 | 9/2008 |
| WO | 2012/027266 A2 | 3/2012 |

OTHER PUBLICATIONS

Im et al., "A Flourescent Rosamine Compound Selectively Stains Pluripotent Stem Cells," with Supporting Information Angewandte Chemie Int. Ed. 49(41):7497-7500 (2010).
Summerhayes el al., "Unusual Retention of Rhodamine 123 by Mitochondria in Muscle and Carcinoma Cells," Proc. Natl. Acad. Sci, USA 79:5292-5296 (1982).
Chang et al., "Stem Cell Detection and Isolation Using Diversity Oriented Fluorescent Library Approach (DOFLA)," Poster Presentation, 8th ISSCR Annual Meeting, San Francisco, CA (Jun. 16-19, 2010).
Kang et al., "Stem Cell Detection and Isolation Using Diversity Oriented Fluorescent Library Approach (DOFLA)," Poster Presentation, 9th ISSCR Annual Meeting, Toronto, Canada (Jun. 15-18. 2011).
Kang et al., "Embryonic and Induced Pluripotent Stem Cell Staining and Sorting with the Live-Cell Fluorescence Imaging Probe CDy1," Nature Protocols 6(7):1044-1052 (2011).
Jiao et al., "Microwave-Assisted Syntheses of Regioisomerically Pure Bromorhodamine Derivatives, " Organic Letters, 5:3675-3677 (2003).
Liu et al., "Rational Design and Synthesis of a Novel Class of Highly Fluorescent Rhodamine Dyes That Have Strong Absorption at Long Wavelengths," Tetrahedron Letters, 44:4355-4359 (2003).

(Continued)

*Primary Examiner* — Marcia S Noble
(74) *Attorney, Agent, or Firm* — LeClairRyan, a Professional Corporation

(57) ABSTRACT

The present invention relates to methods of detecting, in a sample, embryonic stem cells, induced pluripotent stem cells, and/or cells undergoing reprogramming to produce induced pluripotent stem cells. These methods include providing a sample potentially containing such cells and providing a rosamine derivative compound of the formula (I):

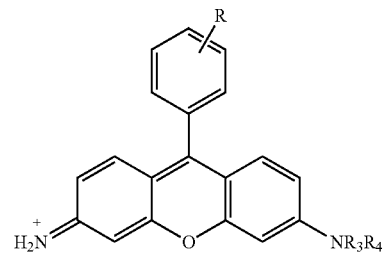

where the rosamine derivative compound selectively produces fluorescent signals for embryonic stem cells, induced pluripotent stem cells, and/or cells undergoing reprogramming to produce induced pluripotent stem cells. These methods also include the steps of contacting the sample with the rosamine derivative compound and detecting the presence of the embryonic stem cells, induced pluripotent stem cells, and/or cells undergoing reprogramming to produce induced pluripotent stem cells based on fluorescent signals emitted by the sample following said contacting.

9 Claims, 14 Drawing Sheets
(12 of 14 Drawing Sheet(s) Filed in Color)

(56) References Cited

OTHER PUBLICATIONS

Li et al., "Solid-Phase Synthesis of Styryl Dyes and Their Application as Amyloid Sensors," Angew Chem. Int. Ed., 43:6331-6335 (2004).

Müller et al., "Interactions of Heteroaromatic Compounds with Nucleic Acids," Eur. J. Biochem 54:279-201 (1975).

International Search Report and Written Opinion for related PCT International Patent Application No. PCT/US2011/048602 (mailed Mar. 20, 2012).

Ahn et al., "Combinatorial Rosamine Library and Application to In Vivo Glutathione Probe," J. Am. Chem. Soc., 129:4510-4511 (2007).

Wagner et al., "Small-Molecule Fluorophores to Detect Cell-state Switching in the Context of High-throughput Screening," with Supporting Information, J. Am. Chem. Soc. 130:4208-09 (2008) (E-published Mar. 8, 2008).

Kang et al., "Diversity-Driven Chemical Probe Development for Biomolecules: Beyond Hypothesis-Driven Approach," Chem. Soc. Rev. 40.3613-3626 (2011).

Kim et al., "Control of Muscle Differentiation by a Mitochondria-Targeted Fluorophore," with Supplementary Information, J. Am. Chem. Soc. 132(2):576-579 (Published online Dec. 18, 2009).

Biiska et al., "Lipoic Acid—The Drug of the Future?," Pharmacol Rep. 57(5):570-577 (2005).

Cho et al., "Alpha-lipoic Acid Inhibits Adipocyte Differentiation by Regulating Pro-Adipogenic Transcription Factors Via Mitogen-activated Protein Kinase Pathways," JBC 278(37):34823-33 (2003).

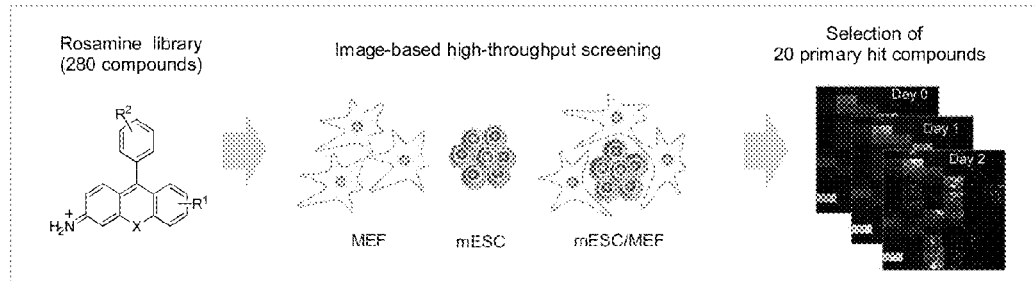
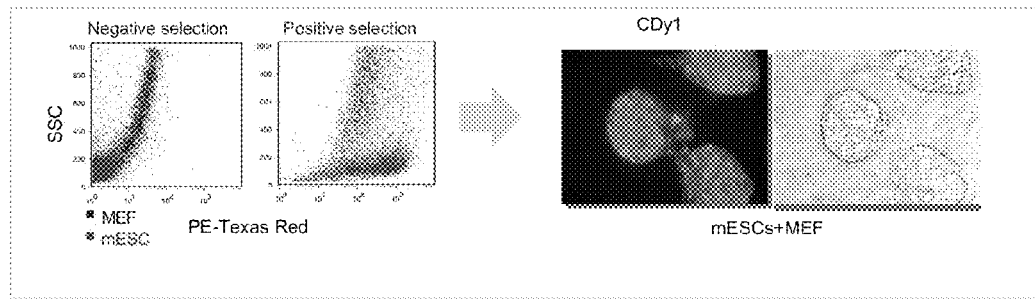
*FIG. 1B*
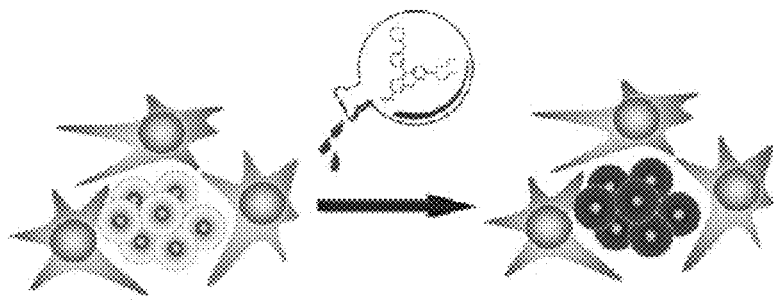
*FIG. 1C*

Characterization of CDy1.
$^1$H-NMR (CDCl$_3$) δ 9.37 (br s, NH), 7.55 (m, 2H), 7.34 (s, 1H), 7.18 (m, 4H), 7.02 (dd, J=1.75, 2.05Hz, 1H), 6.73 (m, 2H), 3.71 (t, J=4.8Hz, 4H), 3.62 (s, 2H), 3.47 (t, J=7.31Hz, 4H), 2.49 (s, 4H), 1.66 (m, 4H), 1.43 (m, 4H), 1.01(t, J=7.02Hz, 6H) $^{13}$C-NMR (CDCl$_3$) δ 160.01, 157.51, 156.38, 153.79, 137.83, 131.18, 130.91, 130.32, 129.66, 128.72, 127.71, 127.17, 117.73, 113.09, 111.77, 111.28, 97.81, 95.61, 65.84, 61.78, 52.53, 50.59, 28.36, 19.13, 12.79ppm. HRMS (ESI): Calculated for C$_{32}$H$_{39}$N$_3$O$_2^+$(M+H)$^+$: 498.67 Found: 498.3115
LC-MS(ESI)
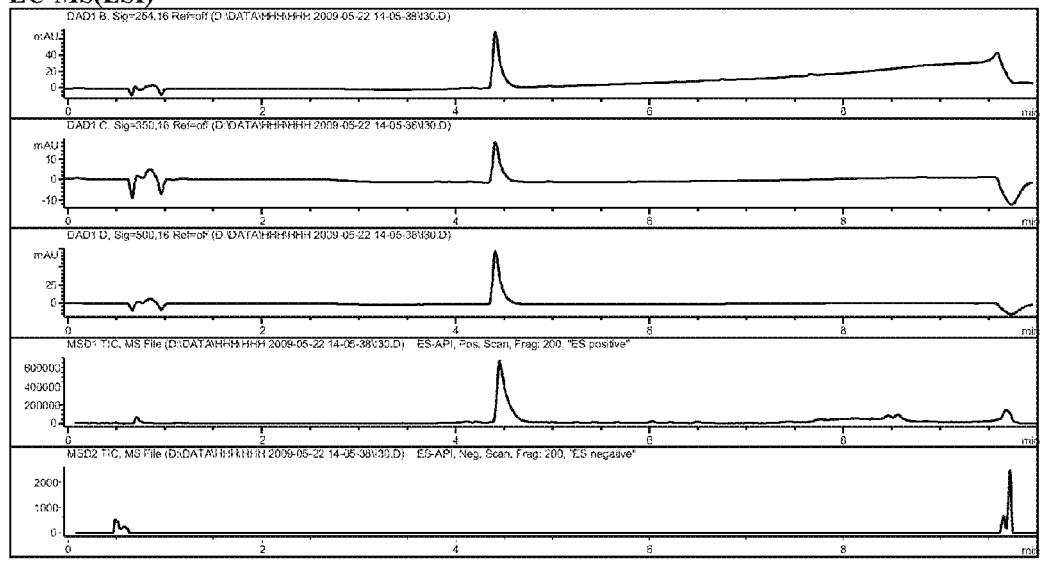
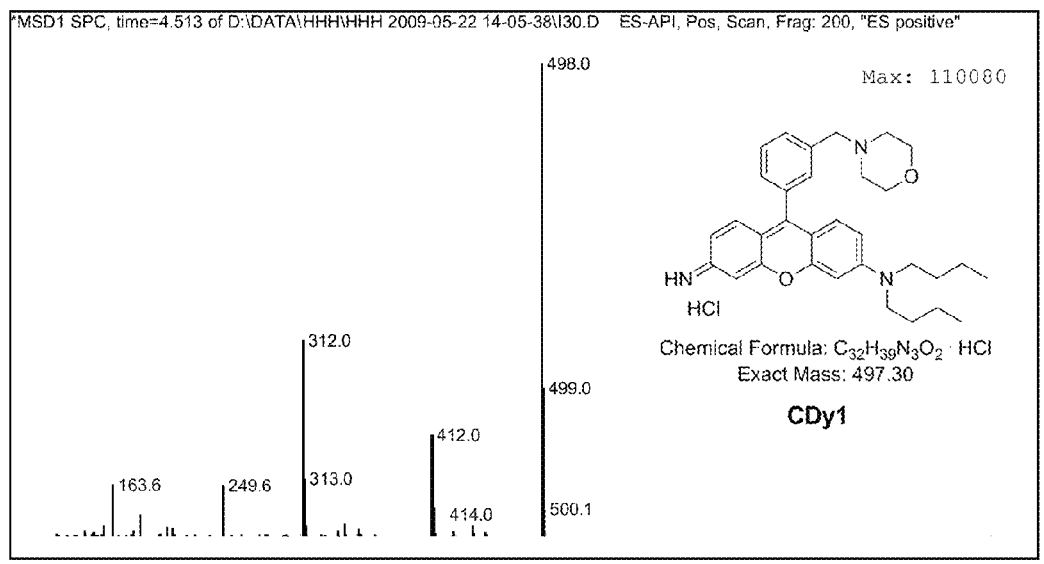
*FIG. 2A*

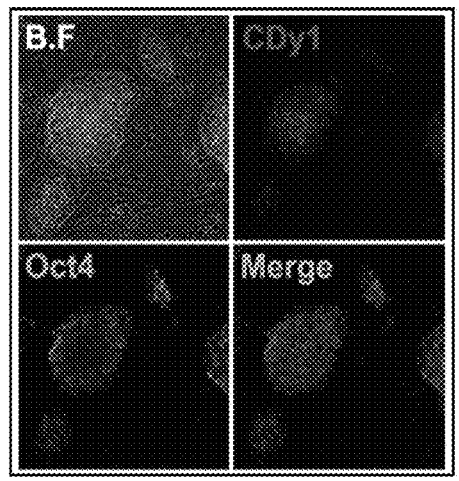
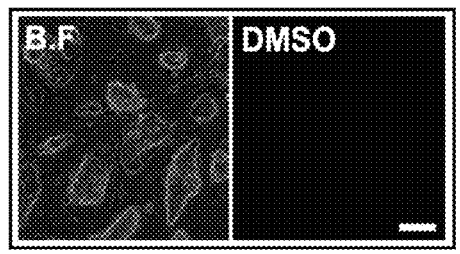
*FIG. 2B*
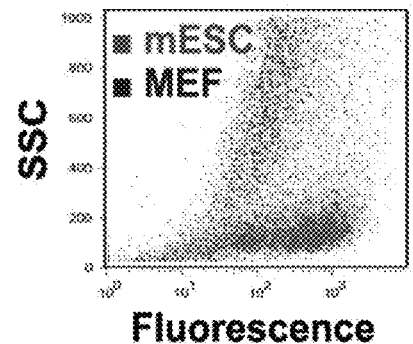
*FIG. 2C*
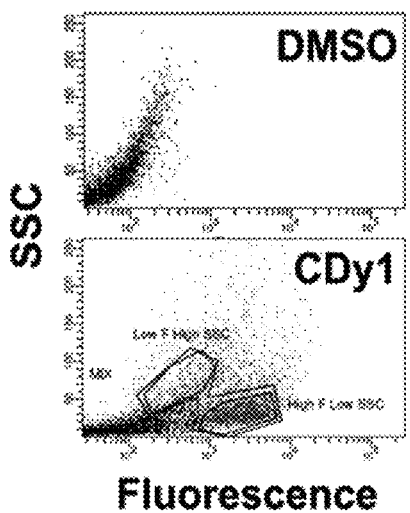
*FIG. 2D*
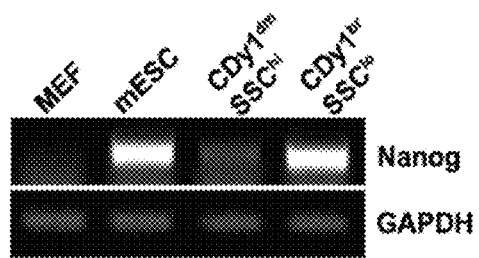
*FIG. 2E*

Reagents and conditions: (i) *p*-methoxybenzylbromide, NaH, THF/DMF; (ii) (3-(((tetrahydro-2*H*-pyran-2-yl)oxy)methyl)phenyl)magnesium bromide, THF and then 1N HCl/THF; (iii) PBr3, DCM; (iv) Amine derivatives, THF; (v) Trifluoroacetic acid.

Table 1: Structure-Selectivity Relationship using flow cytometry in CDy1 analogues*

| Code | Structure | MEF | mESC | mESC/MEF |
|---|---|---|---|---|
| Control | DMSO | 4.5 | 3.1 | 0.7 |
| CDy1 | -N(morpholine) | 8.1 | 99 | 12.2 |
| CDy1-109 | -N(piperazine)-pyridyl | 39.8 | 73.7 | 1.9 |
| CDy1-141 | -N(piperazine)-CH₂CH₂OH | 24.6 | 12.6 | 0.5 |
| CDy1-206 | -N(Me)(CH₂CH=CH₂) | 63.2 | 162.0 | 2.6 |
| CDy1-271 | -N(piperidine) | 23.5 | 33 | 1.4 |
| CDy1-331 | -N(piperazine)-C₆H₄-NO₂ | 32.6 | 47.4 | 1.5 |
| CDy1-353 | -N(piperazine)-cyclohexyl | 36.9 | 67.8 | 1.8 |
| CDy1-520 | -N(piperidine)-OH | 51.7 | 101 | 2.0 |
| CDy1-559 | -N(piperidine)-N(piperidine) | 63.3 | 26.8 | 0.4 |
| CDy1-678 | -N(piperazine)-iPr | 24.7 | 13.5 | 0.6 |
| CDy1-679 | -N(piperidine)-OH | 28.4 | 18.7 | 0.7 |

*: The ratios of mESC to MEF fluorescence mean values obtained from flow cytometry were used for cell selectivity analysis. The cells were incubated with 500 nM of each compound for 1 hr and washed with PBS for flow cytometry.

METHODS FOR DETECTING EMBRYONIC STEM CELLS, INDUCED PLURIPOTENT STEM CELLS, OR CELLS UNDERGOING REPROGRAMMING TO PRODUCE INDUCED PLURIPOTENT STEM CELLS

This application claims the benefit of U.S. Provisional Patent Application Ser. No. 61/376,665, filed Aug. 24, 2010, which is hereby incorporated by reference in its entirety.

FIELD OF THE INVENTION

The present invention generally relates to detection of stem cells in a sample. In particular, the present invention relates to detection of embryonic stem cells, induced pluripotent stem cells, and cells undergoing reprogramming to produce induced pluripotent stem cells in a sample using rosamine compounds.

BACKGROUND OF THE INVENTION

Stem cells, which are capable of self-renewing and differentiating into various types of cells, have captured great interest as a valuable resource for regenerative medicine and developmental biology research. Technical progress during the last decade has enabled the isolation of stem cells from a wide range of tissues, their differentiation into specific types of cells, and the generation of induced pluripotent stem cells ("iPSC") from somatic cells. The recent success of patient-specific iPSC generation (Park et al., "Disease-specific Induced Pluripotent Stem (iPS) Cells," *Cell*, 134(5):877-886 (2008)) and its differentiation into functional cells (Dimos et al., "Induced Pluripotent Stem Cells Generated from Patients with ALS Can Be Differentiated into Motor Neurons," *Science*, 321:1218-1221 (2008)) exemplifies how stem cells can be used for drug discovery and treatment of specific individual patients with complex diseases (Dimos et al., "Induced Pluripotent Stem Cells Generated from Patients with ALS Can Be Differentiated into Motor Neurons," *Science*, 321: 1218-1221 (2008)).

However, despite the general enthusiasm for the multiple applications of stem cells, their practical use both in research and disease therapy has been hampered by the heterogeneity of stem cells and their unpredictable proliferation and differentiation (Amariglio et al., "Donor-Derived Brain Tumor Following Neural Stem Cell Transplantation in an Ataxia Telangiectasia Patient," *PLoS Med.*, 6(2): e1000029 (2009)). The current methods of isolation and characterization of stem cells mostly depend on morphology in culture such as colony or sphere formation and marker protein expression that can be detected by immunostaining. These methods, however, require a long time and antibody reactions which may make the cells unsuitable for further usage. Therefore, the development of tools and technologies that may facilitate the isolation, identification, and characterization of stem cells is one of the most demanding requisites in the field of stem cell research and applications.

The present invention is directed to overcoming these and other deficiencies in the art.

SUMMARY OF THE INVENTION

A first aspect of the present invention is directed to a method of detecting, in a sample, embryonic stem cells or induced pluripotent stem cells. This method includes providing a sample potentially containing embryonic stem cells or induced pluripotent stem cells and providing a rosamine derivative compound of formula (I):

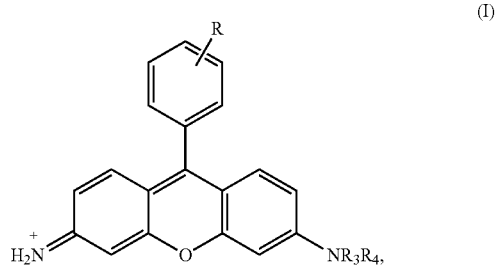

wherein R is —$CH_2NR^1 R^2$;

$R^1$ and $R^2$ are independently H or $C_1$-$C_6$ alkyl; or $R^1$ and $R^2$ form a monocyclic or polycyclic heterocycle containing from 1 to 5 heteroatoms selected from the group consisting of nitrogen, sulfur, and oxygen, wherein the monocyclic or polycyclic heterocycle formed by $R^1$ and $R^2$ is optionally substituted from 1 to 3 times with substituents selected from the group consisting of H, $C_1$-$C_6$ alkyl, OH, $C_3$-$C_6$ cycloalkyl, $C_3$-$C_6$ heterocycle, monocyclic or polycyclic aryl, and monocyclic or polycyclic heteroaryl, wherein $C_1$-$C_6$ alkyl, $C_3$-$C_6$ cycloalkyl, $C_3$-$C_6$ heterocycle, the monocyclic or polycyclic aryl, and the monocyclic or polycyclic heteroaryl are optionally substituted from 1 to 3 times with substituents selected from the group consisting of H, halogen, OH, and $NO_2$; and $R^3$ and $R^4$ are independently H or $C_1$-$C_6$ alkyl; or $R^3$ and $R^4$ form a monocyclic or polycyclic heterocycle containing from 1 to 5 heteroatoms selected from the group consisting of nitrogen, sulfur, and oxygen, wherein the monocyclic or polycyclic heterocycle formed by $R^3$ and $R^4$ is optionally substituted from 1 to 3 times with substituents selected from the group consisting of H, $C_1$-$C_6$ alkyl, OH, $C_3$-$C_6$ cycloalkyl, $C_3$-$C_6$ heterocycle, monocyclic or polycyclic aryl, and monocyclic or polycyclic heteroaryl, wherein $C_1$-$C_6$ alkyl, $C_3$-$C_6$ cycloalkyl, $C_3$-$C_6$ heterocycle, the monocyclic or polycyclic aryl, and the monocyclic or polycyclic heteroaryl are optionally substituted from 1 to 3 times with substituents selected from the group consisting of H, halogen, OH, and $NO_2$. The rosamine derivative compound of formula (I) selectively produces fluorescent signals for embryonic stem cells or induced pluripotent stem cells. This method also includes contacting the sample with the rosamine derivative compound and detecting the presence of the embryonic stem cells or induced pluripotent stem cells based on fluorescent signals emitted by the sample following the contacting.

A second aspect of the present invention relates to a method of detecting, in a sample, cells undergoing reprogramming to produce induced pluripotent stem cells. This method includes providing a sample potentially containing cells undergoing reprogramming to produce induced pluripotent stem cells and providing a rosamine derivative compound of the formula (I):

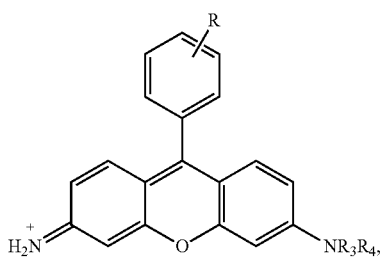

(I)

wherein R is —CH$_2$NR$^1$R$^2$;

R$^1$ and R$^2$ are independently H or C$_1$-C$_6$ alkyl; or

R$^1$ and R$^2$ form a monocyclic or polycyclic heterocycle containing from 1 to 5 heteroatoms selected from the group consisting of nitrogen, sulfur, and oxygen, wherein the monocyclic or polycyclic heterocycle formed by R$^1$ and R$^2$ is optionally substituted from 1 to 3 times with substituents selected from the group consisting of H, C$_1$-C$_6$ alkyl, OH, C$_3$-C$_6$ cycloalkyl, C$_3$-C$_6$ heterocycle, monocyclic or polycyclic aryl, and monocyclic or polycyclic heteroaryl, wherein C$_1$-C$_6$ alkyl, C$_3$-C$_6$ cycloalkyl, C$_3$-C$_6$ heterocycle, the monocyclic or polycyclic aryl, and the monocyclic or polycyclic heteroaryl are optionally substituted from 1 to 3 times with substituents selected from the group consisting of H, halogen, OH, and NO$_2$; and R$^3$ and R$^4$ are independently H or C$_1$-C$_6$ alkyl; or R$^3$ and R$^4$ form a monocyclic or polycyclic heterocycle containing from 1 to 5 heteroatoms selected from the group consisting of nitrogen, sulfur, and oxygen, wherein the monocyclic or polycyclic heterocycle formed by R$^3$ and R$^4$ is optionally substituted from 1 to 3 times with substituents selected from the group consisting of H, C$_1$-C$_6$ alkyl, OH, C$_3$-C$_6$ cycloalkyl, C$_3$-C$_6$ heterocycle, monocyclic or polycyclic aryl, and monocyclic or polycyclic heteroaryl, wherein C$_1$-C$_6$ alkyl, C$_3$-C$_6$ cycloalkyl, C$_3$-C$_6$ heterocycle, the monocyclic or polycyclic aryl, and the monocyclic or polycyclic heteroaryl are optionally substituted from 1 to 3 times with substituents selected from the group consisting of H, halogen, OH, and NO$_2$. The rosamine derivative compound of formula (I) selectively produces fluorescent signals for cells undergoing reprogramming to produce induced pluripotent stem cells. This method also includes contacting the sample with the rosamine derivative compound and detecting the presence of the cells undergoing reprogramming to produce induced pluripotent stem cells based on fluorescent signals emitted by the sample following the contacting.

Fluorescent small molecules have been widely used for the visualization of polymeric biomolecules or cellular organelles (Sutton et al., "Cell Tracking with Optical Imaging" Eur. Radiol., 18(10): 2021-32 (2008), which is hereby incorporated by reference in its entirety). Combinatorial chemistry has been employed to develop several diversity oriented fluorescence libraries ("DOFL") and successfully applied for the discovery of imaging probes for a number of biological targets (Lee et al., "Diversity-oriented Fluorescence Library Approach for the Discovery of Sensors and Probes," Mol. Biosyst., 5:411-421 (2009), which is hereby incorporated by reference in its entirety). Among these libraries is a rosamine library synthesized using solid-phase chemistry (Ahn et al., "Combinatorial Rosamine Library and Application to in Vivo Glutathione Probe," J. Am. Chem. Soc., 129(15): 4510-4511 (2007), which is hereby incorporated by reference in its entirety) to give more flexibility onto the rhodamine scaffold. The rosamine library has excellent photophysical properties and has been used to discover a compound that controls muscle differentiation (Kim et al., "Control of Muscle Differentiation by a Mitochondria-Targeted Fluorophore," J. Am. Chem. Soc. 132(2): 576-579 (2009), which is hereby incorporated by reference in its entirety).

In accordance with the present invention, a combinatorial rosamine library (combinatorial rosamine libraries disclosed in U.S. Patent Application Publication Nos. US 2008/0124751 and US 2009/0227467, which are hereby incorporated by reference in their entirety) was screened in embryonic stem cells ("ESC") and novel fluorescent compounds were discovered, including a compound termed compound of designation yellow 1 (CDy1, λex/λem=535/570 nm), that selectively stain ESC and iPSC. Furthermore, fibroblasts undergoing reprogramming to induced pluripotent stem cells were identified prior to the expression of GFP under control of the Oct4 promoter. The fluorescent bioimaging probes developed in accordance with the present invention are useful tools for, among other things, stem cell research, including ESC and iPSC detection. As shown in the Examples, below, the probes of the present invention can be used for the identification and isolation of live ESC and iPSC without the aid of a genetic reporter system at an earlier stage of reprogramming and during the ESC differentiation. No ESC or iPSC selective fluorescent probe of this type has yet been reported. The probes and methods of the present invention are invaluable for stem cell research and purification or selection of stem cell populations.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

FIG. 1B is a schematic drawing showing rosamine library screening in mouse ESC ("mESC") and mouse embryonic fibroblasts ("MEF"). CDy1 was selected as a final hit compound by image-based screening followed by flow cytometry. In particular, FIG. 1B shows that in the primary screening using image-based analysis, mESC and MEF feeder cells were incubated with 280 rosamine compounds, TRITC fluorescence and bright field images were taken, and 20 compounds that stained mESC consistently with stronger intensity than MEF were manually selected. In the secondary screening, shown in the bottom panel of FIG. 1B, mESC and MEF were incubated separately with each of the hit compounds and then were analyzed using flow cytometry to find CDy1 as the most selective for mESCs among the 20 hit compounds. FIG. 1C is a schematic diagram illustrating a fluorescent rosamine compound (e.g., CDy1) selectively staining a population of stem cells according to the present invention.

FIGS. 2A-2E show the structure and characterization of CDy1, as well as selective staining of mESC by CDy1. FIG. 2A shows the chemical structure of CDy1 in its salt form as well as its chemical characterization. FIG. 2B upper panel is an image showing CDy1-stained mESC that were immunostained with anti-Oct4 antibody (B.F., bright field; scale bar, 100 μm). FIG. 2B lower panel is an image showing DMSO used as a control. FIG. 2C is a flow cytometry dot plot image of CDy1 stained mESC and MEF. Images of pure cell populations were overlaid. FIG. 2D is a flow cytometry dot plot image of mESC and MEF mixed cells incubated with DMSO (upper panel) and mESC and MEF mixed cells incubated with CDy1 (lower panel). FIG. 2E shows a Nanog expression analysis using RT-PCR. SSC$^{low}$ CDy1$^{bright}$ and SSC$^{high}$ CDy1$^{dim}$ cells were sorted from an mESC and MEF mixture after CDy1 staining.

FIG. 5 is a table of flow cytometry results, which show the structure-cell selectivity relationship in CDy1 analogues. The ratios of mESC to MEF fluorescence mean values obtained from flow cytometry were used for cell selectivity analysis. The cells were incubated with 500 nM of each compound for one hour and washed with phosphate buffered saline (PBS) for flow cytometry.

FIG. 10A shows iPSC selective staining by CDy1. At 10 days post infection ("dpi") with Oct4, Sox2, Klf4, and c-Myc, the iPSCs generated from Oct4-GFP transgenic mouse MEF were stained with CDy1 overnight. The pictures shown in FIG. 10A are of the same colony taken at 11 and 12 dpi (B.F, bright field; scale bar, 200 µm). FIG. 10B is a bar graph showing the results of time-course analysis of CDy1-stained colonies. Among the 342 CDy1 positive but GFP negative colonies counted at 10 dpi, 338 colonies expressed GFP at 25 dpi. FIG. 10C shows images that confirm that the cells that expressed GFP at 12 dpi were stained by CDy1 at as early as 6 dpi.

FIG. 15A is graph showing stained and unstained cells collected using FACS at 10 dpi. FIG. 15B shows bright field and fluorescent images of FACS sorted CDy1$^{bright}$ and CDy1$^{dim}$ cells cultured until 24 dpi (B.F, bright field). FIG. 15C is a bar graph showing that CDy1$^{bright}$ cells generated 51 GFP-positive induced pluripotent stem cell colonies per well but no colonies were observed in a CDy1$^{dim}$ cell plated well.

DETAILED DESCRIPTION OF THE INVENTION

Figure 1A:
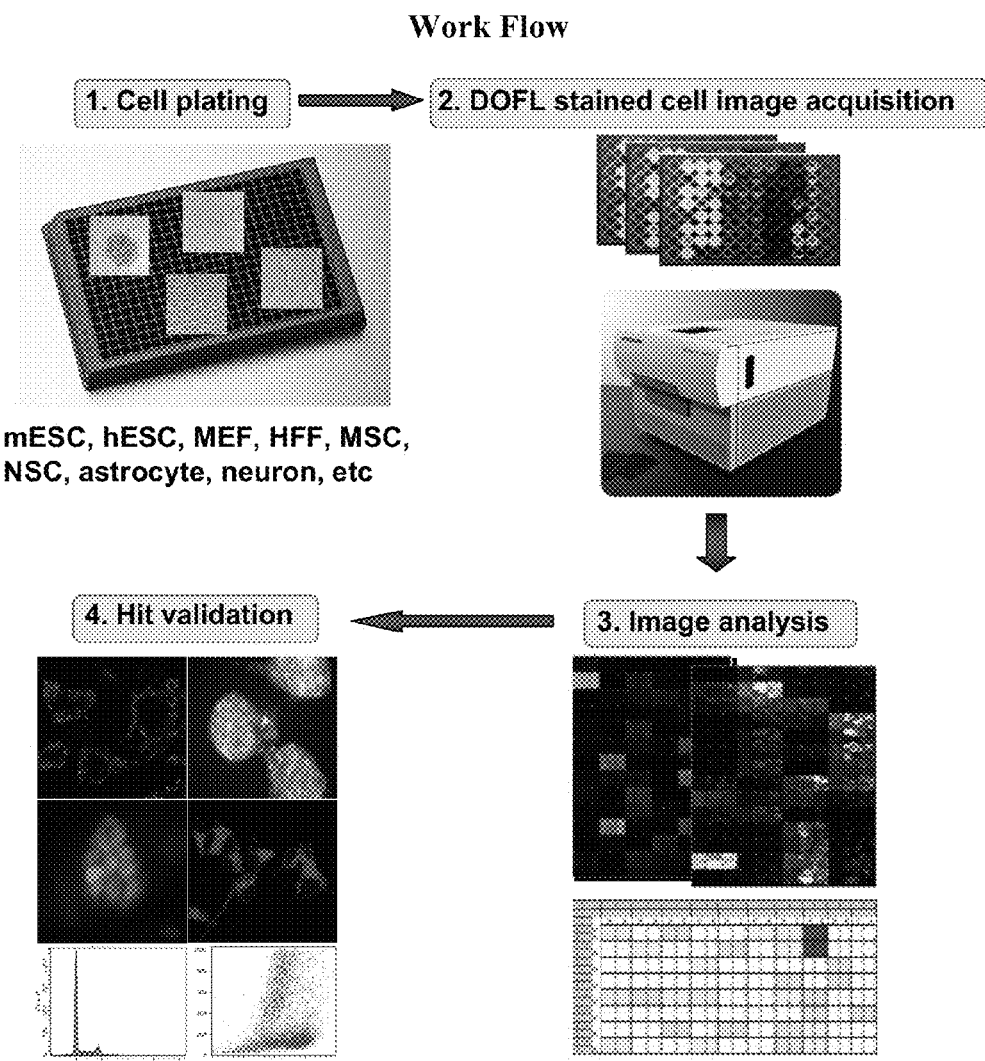
FIG. 1A is a diagram illustrating the workflow used for identification of fluorescent probes of present invention. The diagram shows the steps of cell plating, DOFL stained cell image acquisition, image analysis, and hit validation.
Figure 3:
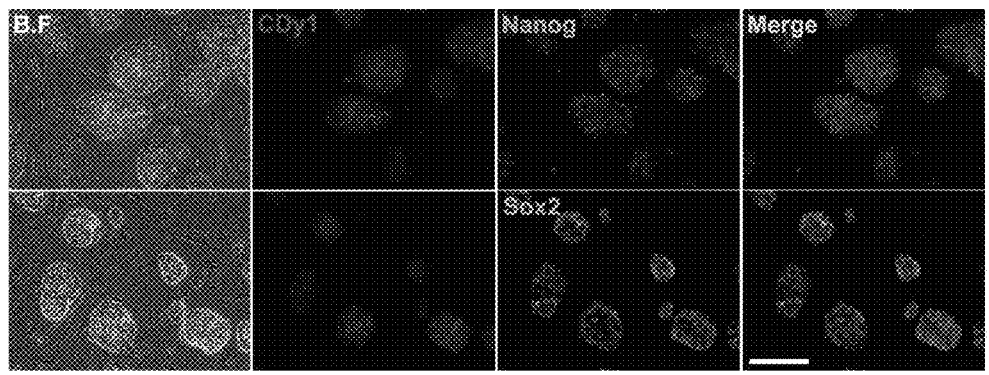
FIG. 3 shows images of CDy1-stained mESC costained with pluripotent stem cell marker antibodies. The expression of Nanog and Sox2 in the CDy1-stained cells was verified by immunofluorescence staining with anti-Nanog or Sox2 antibodies. Scale bar, 200 µm.

A first aspect of the present invention is directed to a method of detecting, in a sample, embryonic stem cells or induced pluripotent stem cells. This method includes providing a sample potentially containing embryonic stem cells or induced pluripotent stem cells and providing a rosamine derivative compound of the formula (I):

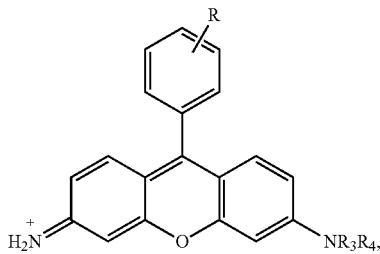

(I)

wherein R is —CH$_2$NR$^1$ R$^2$;
R$^1$ and R$^2$ are independently H or C$_1$-C$_6$ alkyl; or
R$^1$ and R$^2$ form a monocyclic or polycyclic heterocycle containing from 1 to 5 heteroatoms selected from the group consisting of nitrogen, sulfur, and oxygen, wherein the monocyclic or polycyclic heterocycle formed by R$^1$ and R$^2$ is optionally substituted from 1 to 3 times with substituents selected from the group consisting of H, C$_1$-C$_6$ alkyl, OH, C$_3$-C$_6$ cycloalkyl, C$_3$-C$_6$ heterocycle, monocyclic or polycyclic aryl, and monocyclic or polycyclic heteroaryl, wherein C$_1$-C$_6$ alkyl, C$_3$-C$_6$ cycloalkyl, C$_3$-C$_6$ heterocycle, the monocyclic or polycyclic aryl, and the monocyclic or polycyclic heteroaryl are optionally substituted from 1 to 3 times with substituents selected from the group consisting of H, halogen, OH, and NO$_2$; and R$^3$ and R$^4$ are independently H or C$_1$-C$_6$ alkyl; or
R$^3$ and R$^4$ form a monocyclic or polycyclic heterocycle containing from 1 to 5 heteroatoms selected from the group consisting of nitrogen, sulfur, and oxygen, wherein the monocyclic or polycyclic heterocycle formed by R$^3$ and R$^4$ is optionally substituted from 1 to 3 times with substituents selected from the group consisting of H, C$_1$-C$_6$ alkyl, OH, C$_3$-C$_6$ cycloalkyl, C$_3$-C$_6$ heterocycle, monocyclic or polycyclic aryl, and monocyclic or polycyclic heteroaryl, wherein C$_1$-C$_6$ alkyl, C$_3$-C$_6$ cycloalkyl, C$_3$-C$_6$ heterocycle, the monocyclic or polycyclic aryl, and the monocyclic or polycyclic heteroaryl are optionally substituted from 1 to 3 times with substituents selected from the group consisting of H, halogen, OH, and NO$_2$. The rosamine derivative compound of formula (I) selectively produces fluorescent signals for embryonic stem cells or induced pluripotent stem cells. This method also includes contacting the sample with the rosamine derivative compound and detecting the presence of the embryonic stem cells or induced pluripotent stem cells based on fluorescent signals emitted by the sample following the contacting.

Another aspect of the present invention relates to a method of detecting, in a sample, cells undergoing reprogramming to produce induced pluripotent stem cells. This method includes providing a sample potentially containing cells undergoing reprogramming to produce induced pluripotent stem cells and providing a rosamine derivative compound of the formula (I):

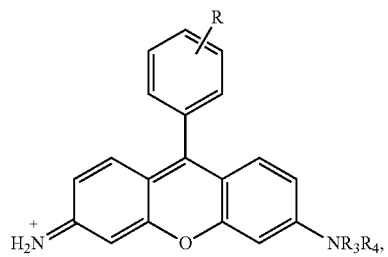

(I)

wherein R is —CH$_2$NR$^1$ R$^2$;
R$^1$ and R$^2$ are independently H or C$_1$-C$_6$ alkyl; or
R$^1$ and R$^2$ form a monocyclic or polycyclic heterocycle containing from 1 to 5 heteroatoms selected from the group consisting of nitrogen, sulfur, and oxygen, wherein the monocyclic or polycyclic heterocycle formed by R$^1$ and R$^2$ is optionally substituted from 1 to 3 times with substituents selected from the group consisting of H, C$_1$-C$_6$ alkyl, OH, C$_3$-C$_6$ cycloalkyl, C$_3$-C$_6$ heterocycle, monocyclic or polycyclic aryl, and monocyclic or polycyclic heteroaryl, wherein C$_1$-C$_6$ alkyl, C$_3$-C$_6$ cycloalkyl, C$_3$-C$_6$ heterocycle, the monocyclic or polycyclic aryl, and the monocyclic or polycyclic heteroaryl are optionally substituted from 1 to 3 times with substituents selected from the group consisting of H, halogen, OH, and NO$_2$; and R$^3$ and R$^4$ are independently H or C$_1$-C$_6$ alkyl; or
R$^3$ and R$^4$ form a monocyclic or polycyclic heterocycle containing from 1 to 5 heteroatoms selected from the group consisting of nitrogen, sulfur, and oxygen, wherein the monocyclic or polycyclic heterocycle formed by R$^3$ and R$^4$ is optionally substituted from 1 to 3 times with substituents selected from the group consisting of H, C$_1$-C$_6$ alkyl, OH, C$_3$-C$_6$ cycloalkyl, C$_3$-C$_6$ heterocycle, monocyclic or polycyclic aryl, and monocyclic or polycyclic heteroaryl, wherein C$_1$-C$_6$ alkyl, C$_3$-C$_6$ cycloalkyl, C$_3$-C$_6$ heterocycle, the monocyclic or polycyclic aryl, and the monocyclic or polycyclic heteroaryl are optionally substituted from 1 to 3 times with substituents selected from the group consisting of H, halogen, OH, and NO$_2$. The rosamine derivative compound of formula (I) selectively produces fluorescent signals for cells undergoing reprogramming to produce induced pluripotent stem cells. This method also includes contacting the sample with the rosamine derivative compound and detecting the presence of the cells undergoing reprogramming to produce induced pluripotent stem cells based on fluorescent signals emitted by the sample following the contacting.

As used above, and throughout the description of the invention, the following terms, unless otherwise indicated, shall be understood to have the following meanings:

The term "alkyl" means an aliphatic hydrocarbon group which may be straight or branched having about 1 to about 6 carbon atoms in the chain. Branched means that one or more lower alkyl groups such as methyl, ethyl, or propyl are attached to a linear alkyl chain. Representative alkyl groups include methyl, ethyl, n-propyl, i-propyl, n-butyl, t-butyl, n-pentyl, and 3-pentyl and the like.

When an alkyl is substituted from 1 to 3 times with halogen, the substituted groups include CF$_3$, CF$_2$H, CH$_2$CF$_3$, CH$_2$CF$_2$H, and the like.

The term "cycloalkyl" means a non-aromatic monocyclic ring system of about 3 to about 8 carbon atoms. Representative monocyclic cycloalkyl include cyclopropyl, cyclobutyl, cyclopentyl, cyclohexyl, cycloheptyl, and the like.

The term "halo" or "halogen" means fluoro, chloro, bromo, or iodo.

The term "aryl" means an aromatic monocyclic or polycyclic ring system of 6 to about 14 carbon atoms, preferably 6 to about 10 carbon atoms. In the case of a polycyclic ring system, only one of the rings needs to be aromatic for the ring system to be defined as "aryl". Representative aryl groups include phenyl, naphthyl, indenyl, indanyl, and the like.

The term "heteroaryl" means an aromatic monocyclic or polycyclic ring system of 6 to about 14 carbon atoms, preferably 5 to 10 carbon atoms, in which one or more of the atoms in the ring system is/are element(s) other than carbon, for example, nitrogen, oxygen, or sulfur. In the case of polycyclic ring systems, only one of the rings needs to be aromatic for the ring system to be defined as "heteroaryl". The prefix aza, oxa, or thio before heterocycle means that at least a nitrogen, oxygen, or sulfur atom, respectively, is present as a ring atom. A nitrogen atom of a heteroaryl is optionally oxidized to the corresponding N-oxide. A sulfur atom of a heteroaryl is optionally oxidized to the corresponding sulfoxide or sulfone. Representative aromatic monocyclic ring systems include pyrrole, 1H-pyrazole, pyridinyl, pyrimidinyl, pyridazinyl, pyrazinyl, triazinyl, pyranyl, furanyl, pyrrolyl, thiophenyl, pyrazolyl, imidazolyl, oxazolyl, isoxazolyl, thiazolyl, isothiazolyl, 1H-1,2,3-triazolyl, 2H-1,2,3-triazolyl, 4H-1,2,4-triazolyl, oxadiazolyl, thiadiazolyl, tetrazolyl, and the like. Representative aromatic polycyclic ring systems include quinoline, isoquinoline, quinoxaline, quinazoline, cinnoline, acridine, and the like. For lactam analogues of "aromatic monocyclic heterocycles" such as pyridin-2(1H)-one, pyridazin-3(2H)-one, and the like, when these lactams are structurally connected through the nitrogen atom adjacent to the lactam carbonyl, these lactams of aromatic monocyclic heterocycles are considered as "aromatic monocyclic heterocycles" in this invention. In addition, when a nitrogen containing heterocycle is substituted by hydroxyl group on the carbon adjacent to the nitrogen, the substituted heterocycle can be named as either tautomer.

The term "heterocycle" means a monocyclic ring system of about 4 to 8 ring atoms, preferably 5 or 6, or polycyclic ring system of about 8 to 14 ring atoms, preferably 9 or 10, in which one or more of the atoms in the ring system is/are element(s) other than carbon, for example, nitrogen, oxygen, or sulfur. One or multiple rings may be aromatic. The prefix aza, oxa, or thio before the heterocycle means that at least a nitrogen, oxygen, or sulfur atom, respectively, is present as a ring atom. A nitrogen atom in the ring is optionally oxidized to the corresponding N-oxide. A sulfur atom of a heterocycle is optionally oxidized to either the sulfoxide or sulfone. Representative monocyclic heterocycles include piperidine, piperazine, pyrimidine, morpholine, thiomorpholine, pyrrolidine, tetrahydrofuran, pyran, tetrahydropyran, oxetane, and the like. Representative polycyclic heterocycles include indole, isoindole, indolizine, quinoline, isoquinoline, purine, carbazole, dibenzofuran, chromene, xanthene, and the like.

The term "substituted" or "substitution" of an atom or group means that one or more hydrogen on the designated atom or group is replaced with a selection from the indicated group, provided that the designated atom's normal valency is not exceeded. "Unsubstituted" atoms bear all of the hydrogen atoms dictated by their valency. When a substituent is keto or oxo (i.e., =O), then two hydrogens on the atom are replaced. When a substituent is thio (i.e., =S), then two hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture. As used herein, when an atom or group is optionally substituted multiple times, each such substitution is independently selected.

The term "compounds of the invention" or "rosamine derivative compound", and equivalent expressions, are meant to embrace compounds of general formula (I) as hereinbefore described and their salts.

The term "pluripotent" as used herein refers to a cell with the capacity, under different conditions, to differentiate to cell types characteristic of all three germ cell layers. Pluripotency is also evidenced by the expression of embryonic stem (ES) cell markers, although the preferred test for pluripotency is the demonstration of the capacity to differentiate into cells of each of the three germ layers.

The term "reprogramming" as used herein refers to the process of altering the differentiated state of a terminally-differentiated somatic cell to a pluripotent phenotype.

In accordance with the present invention, a sample potentially containing embryonic stem cells, induced pluripotent stem cells, or cells undergoing reprogramming to produce induced pluripotent stem cells is provided. The sample may include a quantity of cells which contains, or is suspected of containing, one or more undifferentiated and/or differentiated induced pluripotent stem cells, embryonic stem cells, or cells undergoing reprogramming to produce induced pluripotent stem cells. The sample may be a culture of cells grown in vitro. For example, the culture may comprise a suspension of cells or cells cultured in a culture plate or dish. The sample may include a mixed cell population, as described below.

In some embodiments, the sample contains undifferentiated non-induced pluripotent cells, e.g., embryonic stem cells. In other embodiments, the sample contains non-induced pluripotent cells that have undergone differentiation or are undergoing differentiation. In yet other embodiments, the sample contains undifferentiated non-induced pluripotent cells and non-induced pluripotent cells that have undergone differentiation or are undergoing differentiation.

In further embodiments, the sample contains undifferentiated induced pluripotent stem cells. In other instances, the sample may contain induced pluripotent stem cells that have been induced to differentiate into other cells. In yet other embodiments, the sample contains undifferentiated induced pluripotent stem cells and induced pluripotent stem cells that have undergone differentiation or are undergoing differentiation.

In some embodiments, the sample contains cells undergoing reprogramming to produce induced pluripotent stem cells.

In some instances, the sample has been derived from somatic cells that have been induced to pluripotency.

The sample may be one in which undifferentiated pluripotent stem cells have been induced to differentiate into particular cell lineages and therefore the sample may contain a mixture of undifferentiated and differentiated cells. Typically, in such a sample the undifferentiated pluripotent stem cells constitute a few percent of the total number of cells. Removal (or destruction) of the undifferentiated pluripotent stem cells from (or in) such a sample will be useful prior to the clinical application of the sample which contains differentiated cells because, potentially, the undifferentiated cells can form undesirable teratomas. Typically, at least 95% of the undifferentiated pluripotent stem cells are removed or destroyed. In one embodiment, all of the undifferentiated cells are removed or destroyed.

In some embodiments, the sample does not contain non-induced pluripotent cells, e.g. embryonic stem cells (ESCs).

In some embodiments the sample does not contain human embryonic stem cells or non-induced human pluripotent cells.

The sample may contain other non-pluripotent cells, e.g., feeder cells or fibroblasts.

In one embodiment of the present invention, $R^1$ and $R^2$ of the rosamine derivative compound of the formula (I) form an optionally substituted monocyclic heterocycle. In another embodiment of the present invention, $R^1$ and $R^2$ of the rosamine derivative compound of the formula (I) form an optionally substituted monocyclic heterocycle selected from the group consisting of piperidine, piperazine, and morpholine. In a further embodiment of the present invention, the optionally substituted monocyclic heterocycle is morpholine.

In accordance with another embodiment of the present invention, $R^3$ and $R^4$ of the rosamine derivative compound of the formula (I) are each —$CH_2CH_2CH_2CH_3$.

In accordance with a further embodiment of the present invention, $R^3$ and $R^4$ of the rosamine derivative compound of the formula (I) form an optionally substituted monocyclic heterocycle. In another embodiment of the present invention, $R^3$ and $R^4$ of the rosamine derivative compound of the formula (I) form an optionally substituted monocyclic heterocycle selected from the group consisting of piperidine, piperazine, and morpholine. In yet another embodiment of the present invention, the optionally substituted monocyclic heterocycle is piperidine.

In a further embodiment of the present invention, the rosamine derivative compound is

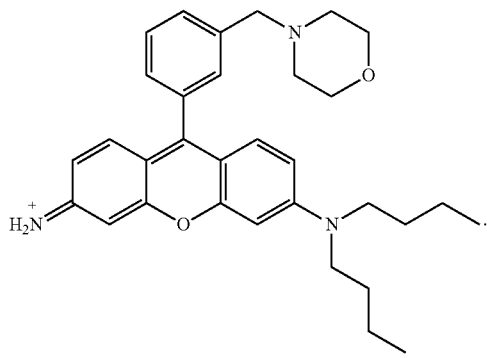 [SMILES: CCCCN(CCCC)c1ccc2c(-c3cccc(CN4CCOCC4)c3)c3ccc(=N)cc-3oc2c1]

Throughout the present application, this compound is also referred to as CDy1.

In another embodiment of the present invention, the rosamine derivative compound is

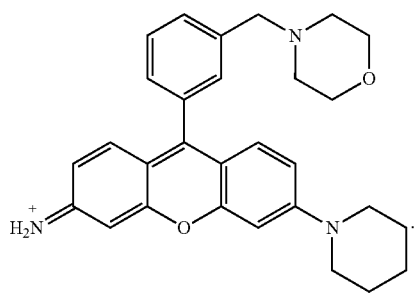 [SMILES: N=c1ccc2c(-c3cccc(CN4CCOCC4)c3)c3ccc(N4CCCCC4)cc3oc-2c1]

In yet another embodiment, the rosamine derivative compound targets mitochondria in embryonic stem cells.

In accordance with the present invention, the sample is contacted with the rosamine compound of the present invention. Contacting may be carried out under conditions effective to produce differing fluorescent signals for the undifferentiated embryonic stem cells or induced pluripotent stem cells than for one or more differentiated forms of the embryonic stem cells or induced pluripotent stem cells, if present in the sample.

In this embodiment, the rosamine derivative compound has a first fluorescent characteristic when bound to undifferentiated embryonic stem cells or induced pluripotent stem cells and a second fluorescent characteristic when bound to one or more differentiated forms of the embryonic stem cells or induced pluripotent stem cells. This embodiment may also involve contacting the rosamine derivative compound with the sample under conditions effective to permit binding of the undifferentiated stem cell or differentiated form of the stem cell present in the sample to the rosamine derivative compound and detecting the presence of the undifferentiated stem cell or differentiated form of the stem cell in the sample as a function of the fluorescence characteristic of the rosamine derivative compound. In this embodiment, the presence of the undifferentiated stem cell is indicated by detection of the first fluorescent characteristic and the presence of the differentiated form of the stem cell is indicated by detection of the second fluorescence characteristic.

In another embodiment of the present invention, the rosamine derivative compound of formula (I) has a first fluorescent characteristic when bound to the embryonic stem cells or induced pluripotent stem cells or cells undergoing reprogramming to produce induced pluripotent stem cells and a second fluorescent characteristic in an unbound state. This embodiment also may include contacting the rosamine derivative compound with the sample under conditions effective to permit binding of any embryonic stem cells or induced pluripotent stem cells or cells undergoing reprogramming to produce induced pluripotent stem cells present in the sample to the rosamine derivative compound and detecting the presence of the target molecule in the sample as a function of the fluorescence characteristic of the rosamine derivative compound. The presence of the embryonic stem cells or induced pluripotent stem cells or cells undergoing reprogramming to produce induced pluripotent stem cells is indicated by detection of the first fluorescent characteristic while the absence of the embryonic stem cells or induced pluripotent stem cells or cells undergoing reprogramming to produce induced pluripotent stem cells is indicated by detection of the second fluorescence characteristic.

Any of the embodiments of the present invention described above may also include exposing the cells to activating radiation, whereby any of the rosamine derivative compounds bound to the cells fluoresce. As a result, an image of the cells based on their fluorescent emission is produced.

Methods of detection and measurement of fluorescent signals in accordance with the present invention are known to those of skill in the art. For example, fluorescent microscopy, flow cytometry, and fluorescence activate cell sorting can all be used in accordance with the present invention.

In addition, any of the embodiments of the present invention described above may also include isolating the embryonic stem cells, induced pluripotent stem cells, or cells undergoing reprogramming to produce induced pluripotent stem cells from the sample.

Embryonic and other pluripotent stem cells have great potential in therapy. Such cells can be used in regenerative medicine to repair tissues which have been damaged by disease or injury. However, the use of embryonic stem cells in medicine is limited due to the significant ethical concerns associated with the use of human embryos. Human fibroblasts can be reprogrammed by the transient overexpression of a small number of genes into induced pluripotent stem cells which functionally and phenotypically resemble human embryonic stem cells.

Although undifferentiated pluripotent stem cells themselves may be used in cell therapy, it is considered to be beneficial to use cells which have started to differentiate, or are differentiated. Methods of encouraging undifferentiated human pluripotent stem cells to differentiate into particular cell lineages are well known in the art. Once this differentiation process has started or proceeded, it is beneficial to remove or destroy undifferentiated pluripotent stem cells which may otherwise form undesirable teratomas.

Thus, it can be seen that it is useful to identify or isolate undifferentiated human pluripotent stem cells (since they can be used themselves in therapy or can be encouraged to differentiate into a particular cell lineage which can be used in therapy). It is also useful to remove or destroy undifferentiated human pluripotent stem cells from a mixture of cells where some of the cells have started to differentiate, or are differentiated, since these differentiated cells are useful in therapy.

Understanding cellular and molecular mechanisms involved in the generation of iPSC is essential to further improve iPS cell technology. However, the mechanistic knowledge of reprogramming, especially at the early stage, is highly limited because only a small number of cells out of heterogeneous cell populations develop into iPS cells and those cells need to be isolated for cellular and molecular mechanism analysis.

The compounds of the present invention, including CDy1, are unique tools to label live cells undergoing reprogramming even before the expression of currently available genetic marker such as Oct4, which is expressed relatively late stage of reprogramming (see FIG. 1C). Thus, global gene expression analysis of the cells isolated at very early stages of reprogramming provides information to identify key molecules or pathways that play important roles in cellular reprogramming.

EXAMPLES

The following examples are provided to illustrate embodiments of the present invention but are by no means intended to limit its scope.

Materials and Methods Used in Examples 1 to 5
Cell Culture

Mouse ESC ("mESC") were cultured in a culture dish coated with 0.1% gelatin using a high-glucose Dulbecco's Modified Eagle's medium (DMEM) supplemented with 10% fetal calf serum, 2 mM L-glutamine, 100 U/ml penicillin, 100 μg/ml streptomycin, 0.1 mM non-essential amino acids, 0.1% β-mercaptoethanol, and 100 U/ml leukemia inhibitory factor (LIF, Chemicon (Millipore), Billerica, Mass.). Mouse embryonic fibroblasts ("MEF") were maintained in the same media as used for mESC without LIF and treated with mitomycin C (10 μg/ml) before being used as feeder cells. Human ESC ("hESC") BG01V purchased from ATCC (ATCC Accession No.: SCRC-2002™) was cultured on mitotically inactivated MEF in DMEM/F12 media supplemented with 20% knock out serum replacement, 1 mM L-glutamine, 0.1 mM β-mercaptoethanol, 1% nonessential amino acid, and 5 ng/ml basic fibroblast growth factor. A human lung cancer cell line H522 was cultured in RPMI 1640 supplemented with 1 mM sodium pyruvate, 100 U/ml penicillin, 100 μg/ml streptomycin, and 5% (v/v) fetal bovine serum (Gibco BRL, Life Technologies, Carlsbad, Calif.).

Flow Cytometry and FACS

MEFs and mESCs were cultured in 60 mm culture dishes for 24 hours in the presence of 500 nM of hit compounds including CDy1. The cells were harvested by trypsin treatment, washed with PBS, and resuspended in PBS. The fluorescence intensity of the cells was measured with flow cytometry (BD™ LSR II) with PE-Texas Red filter (excitation at 488 nm, emission at 615 nm). The dot plot images for each cell type were overlaid using FlowJo7 (Tree Star Inc., Ashland, Oreg.). For FACS, MEF and mESC were cultured in the same dish and the sample was prepared as described above for flow cytometry. The cells were gated into $SSC^{low}$ $CDy1^{bright}$ and $SSC^{high}$ $CDy1^{dim}$ regions and were collected using a FACS machine (BD FACS Aria™, BD Biosciences, Franklin Lakes, N.J.).

RT-PCR

Total RNA was isolated from cells using RNeasy Mini Kit (QIAGEN Inc.) according to the manufacturer's instruction. cDNA was synthesized from 1 μg of total RNA using REVERTAID™ H Minus First strand cDNA Synthesis kit (Fermentas, Glen Burnie, Md.) and amplified by PCR using GOTAQ® Green Master Mix (Promega, Fitchburg, Wis.). The PCR conditions were as follows: 30 seconds denaturation at 95° C., 30 seconds annealing at 60° C., and a final 30 seconds of extension at 72° C. The sequences of primers used in this study are: Nanog (GenBank Accession No. NM_028016.1): sense 5'-AGGGTCTGCTACTGAGAT-GCTCTG-3' (SEQ ID NO:1), antisense 5'-CAACCACTG-GTTTTTCTGCCACCG-3' (SEQ ID NO:2); GAPDH (GenBank Accession No. XM_001473443.1): sense 5'-GCACAGTCAAGGCCGAGAAT-3' (SEQ ID NO:3), antisense 5'-GCCTTCTCCATGGTGGTGAA-3' (SEQ ID NO:4). The PCR products obtained after 25 cycles were resolved on 1% agarose gels, visualized by ethidium bromide staining, and the images were taken using a Gel Logic 200 Imaging System (Kodak, Rochester, N.Y.).

Immunofluorescence Staining

The cells were fixed with 4% paraformaldehyde for 10 minutes, permeabilized with 0.1% TritonX-100/PBS for 10 minutes, and blocked with 2% bovine serum albumin/PBS for one hour. They were incubated with mouse monoclonal antibody against Nestin (diluted 1:500, Millipore, Billerica, Mass.), rabbit polyclonal antibody against Oct4 (diluted 1:300, Abcam, Cambridge, Mass.), mouse monoclonal antibody against SMA (diluted 1:1000, Abcam, Cambridge, Mass.), goat polyclonal antibody against Sox17 (diluted 1:50, R&D Systems, Minneapolis, Minn.), mouse monoclonal antibody against SSEA-1 (diluted 1:100, Millipore, Billerica, Mass.), and mouse monoclonal antibody against TRA-1-60 (diluted 1:100, Millipore, Billerica, Mass.) in PBS overnight at 4° C. The specific binding of primary antibodies was visualized by incubation with Cy5-conjugated goat anti-mouse (diluted 1:500, Invitrogen, Carlsbad, Calif.), Cy5-conjugated goat anti-rabbit (diluted 1:500, Invitrogen, Carlsbad, Calif.), or ALEXA FLOUR® 594 donkey anti-goat (diluted 1:300, Invitrogen, Carlsbad, Calif.) antibodies in PBS for two hours at room temperature.

Alkaline Phosphatase Assay

Induced pluripotent stem cells (iPSCs) in a 6-well plate were fixed with 4% paraformaldehyde for one minute, rinsed with PBS, and stained with Naphthol/Fast Red Violet (NFV) Solution (Millipore, Billerica, Mass.) according to manufacturer's instruction. After incubation in the dark at room temperature for fifteen minutes, the cells were rinsed with PBS. The images were acquired using AZ100 microscope (Nikon, Tokyo, Japan).

iPSC Generation

The retroviral packaging cell, PlatE cell, was maintained in DMEM containing 10% FBS, 100 U/ml penicillin, 100 μg/ml streptomycin, 10 μg/ml blasticidin S, and 1 μg/ml puromycin. For the generation of retroviruses, 40 μg of each retroviral vector expressing each mouse Oct4, Sox2, Klf4, and c-Myc was transfected together using Lipofectamine™ 2000 (Invitrogen, Carlsbad, Calif.) into PlatE cells plated at a density of 8×106 cells/10 cm cell culture dish and cultured overnight in DMEM containing 10% FBS. Medium was changed five hours after transfection to normal maintenance medium and incubated further in a humidified atmosphere of 5% $CO_2$ and 95% air at 37° C. Culture supernatant was harvested 48 hours after transfection, filtered through a 0.45 μm syringe filter, concentrated by using amicon ultra-15 Centrifugal filter units (Millipore, Billerica, Mass.), and stored at −80° C. until use. For reprogramming, MEFs prepared from E13.5 B6; CBA-Tg(Pou5f1-EGFP)$_2$Mnn/J mouse (Jackson Laboratory, Bar Harbor, Me.) embryo were infected with retrovirus mixture eight hours later. Polybrene (Sigma-Aldrich, St. Louis, Mo.) was added at a concentration of 10 μg/ml to increase virus adsorption. Infected MEFs were harvested 48 hours later by trypsinization and plated onto mytomycin C treated MEF feeder cells. The cells were maintained in mESC culture medium that was changed every day until designated time points.

Example 1

CDy1 is Selective for Embryonic Stem Cells

Figure 4:
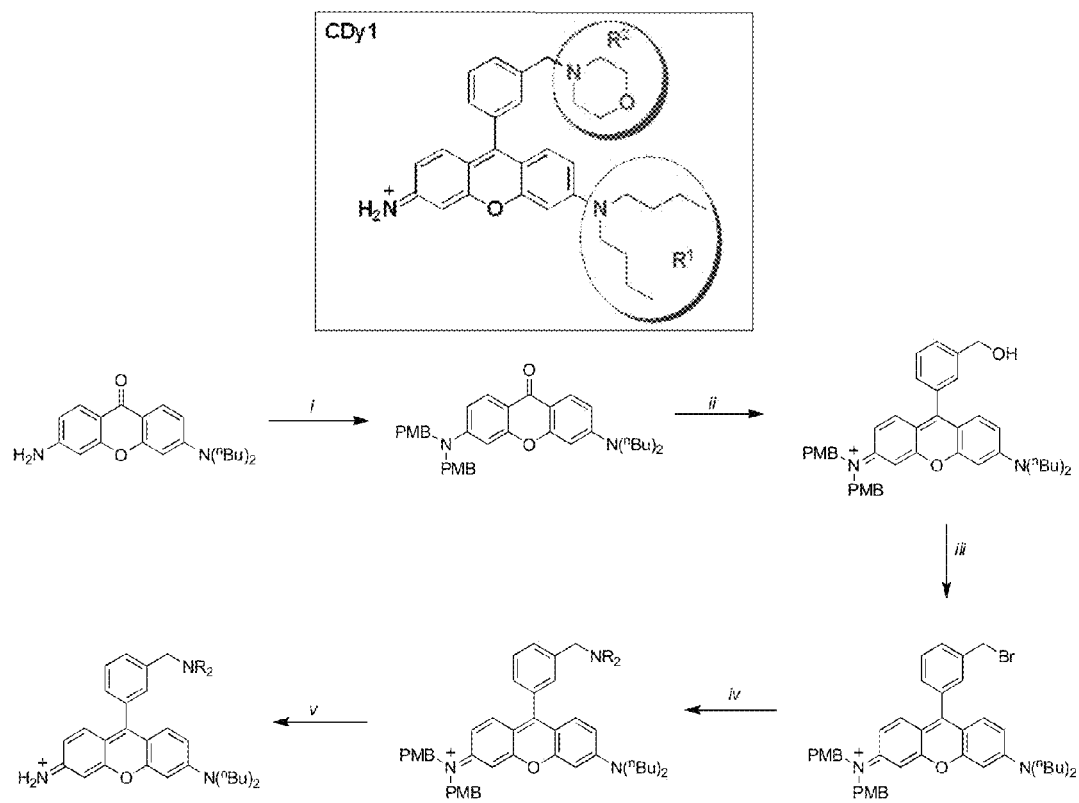
FIG. 4 shows the synthesis of a number of CDy1 analogues by modifying the morpholine group.
Figure 6:
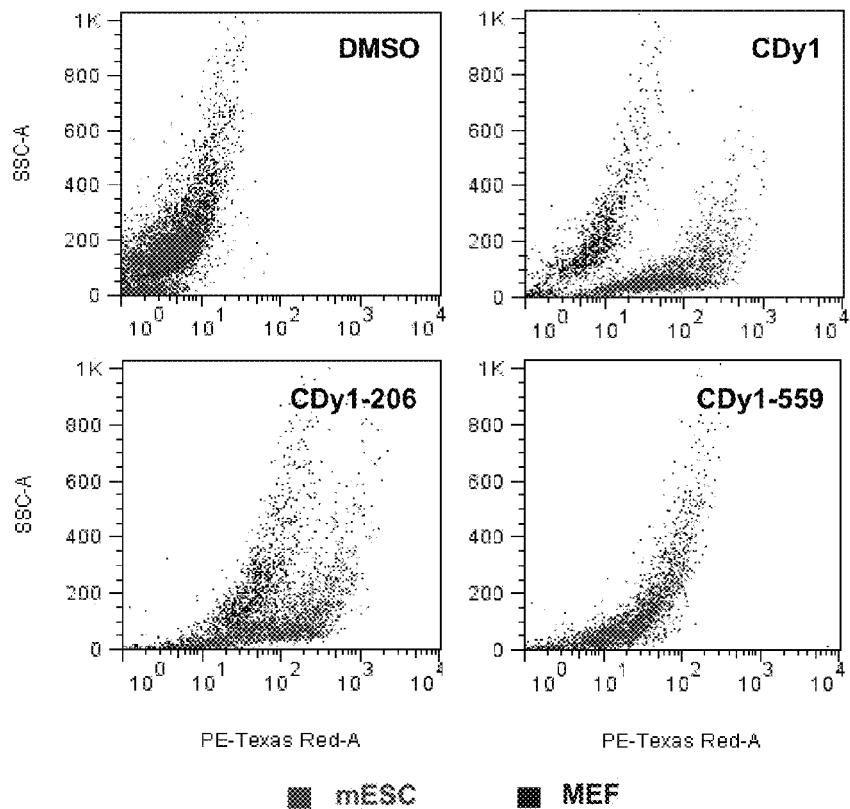
FIG. 6 shows dot plot images of flow cytometry analysis of CDy1 analogues. mESC and MEF were incubated with 500 nM of ten CDy1 analogues for one hour and washed with PBS for flow cytometry. CDy1 was the most selective compound among those tested. Dot plot images of CDy1-206 and CDy1-559 stained cells are displayed as representative images.

For a high-throughput screening, mESC and MEF feeder cells were incubated with 280 rosamine compounds at a concentration of 500 nM in 384-well microplates. After 0.5 hours, 24 hours, and 48 hours, TRITC fluorescence and bright field images were taken using an ImageXpress$^{MICRO}$ imaging system. From the image-based primary screening, 20 compounds that stained mESC consistently with stronger intensity than MEF were manually selected. As a secondary screening, mESC and MEF were incubated separately with each of the hit compounds and these were analyzed using flow cytometry (see work flow set out in FIGS. 1A-1B; results shown in FIGS. 2A-2C and FIG. 3). The compound designated CDy1 (shown in FIG. 2A) was identified as the most selective for mESCs among the 20 hit compounds. For a more systematic structure selectivity relationship study, a number of CDy1 analogues were synthesized by modifying the morpholine group (FIG. 4) based on the finding that most of the 20 primary hits had a di-n-butyl group. The mESC selectivity of all the analogues were, however, much lower than CDy1 which showed 12.2-fold higher intensity in mESC than in MEF. This result suggested that the morpholine group was important for ESC selectivity of CDy1 (see FIG. 5 and FIG. 6).

Example 2

Evaluation of CDy1 with a Mixed Cell Population

Figure 7:
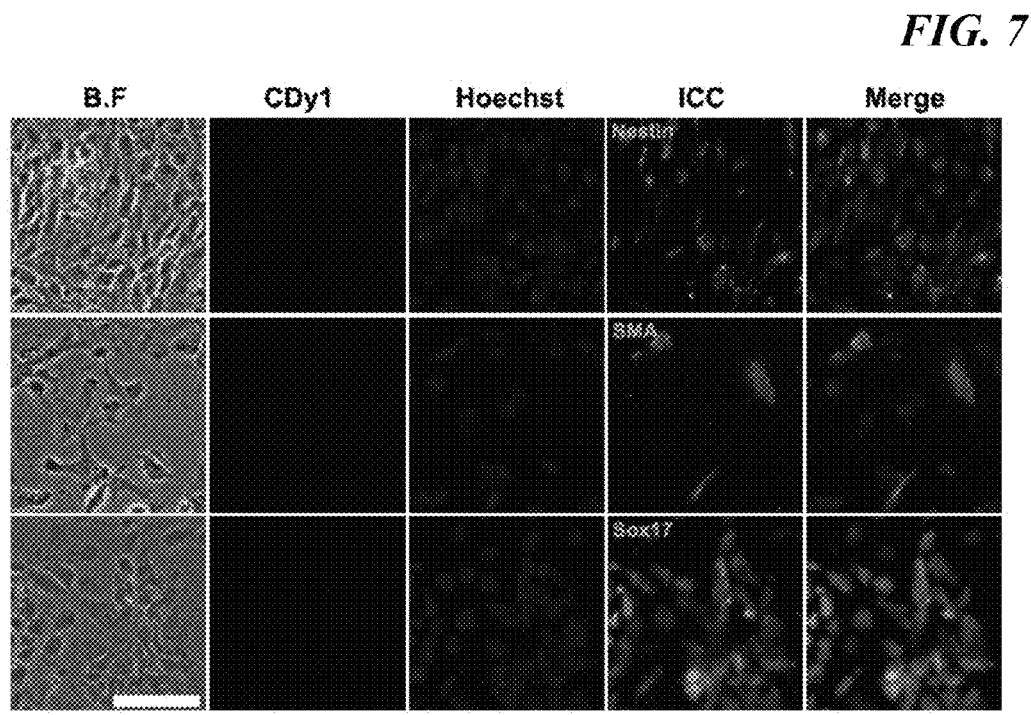
FIG. 7 shows images of CDy1-positive mESC differentiation into lineage specific cells. CDy1-stained mESC were sorted by FACS from an MEF and mESC mixture and allowed to form embryoid bodies in the media without leukemia inhibitory factor ("LIF"). After two weeks, the embryoid bodies were transferred to a gelatin-coated 12-well plate to allow them to attach and grow in monolayer for a further three days. The cells were incubated with CDy1 in the same manner as for mESC, but were not stained. The expression of three germ layer markers Nestin (ectoderm), alpha-smooth muscle (SMA, mesoderm), and Sox17 (endoderm) was detected by immunofluorescence staining (B.F, bright field; ICC, immunocytochemistry; SMA, alpha smooth muscle actin; Scale bar, 100 µm).

To evaluate the capability of CDy1 to isolate ESC from a mixed cell population, a MEF and mESC mixture was stained with CDy1, the mixed cells were gated into $SSC^{low}$ $CDy1^{bright}$ and $SSC^{high}$ $CDy1^{dim}$ regions, and 40,000 cells were collected by FACS from each gate for a stem cell marker Nanog gene expression analysis and colony forming assay. The dot plot image of the CDy1-stained mixed cells was similar to the overlay image of pure populations, whereas the cells incubated with dimethyl sulfoxide used as control were not distinguishable (FIG. 2D). RT-PCR analysis clearly showed that Nanog expression in $SSC^{low}$ $CDy1^{bright}$ cells was much higher than in $SSC^{high}$ $CDy1^{dim}$ cells (FIG. 2E), and the numbers of colonies counted after three days culture were 604 and 6, respectively. Differentiation of these CDy1-stained mESC was induced by culturing media without leukemia inhibitory factor ("LIF"). After two weeks of differentiation, the expression of ectoderm, mesoderm, and endoderm markers was verified by immunocytochemistry (FIG. 7). These data demonstrate that CDy1 can be used for mESC enrichment from a mixed cell population without affecting the properties of stem cells.

Example 3

CDy1 Selectively Stains Induced Pluripotent Stem Cells

Figure 8:
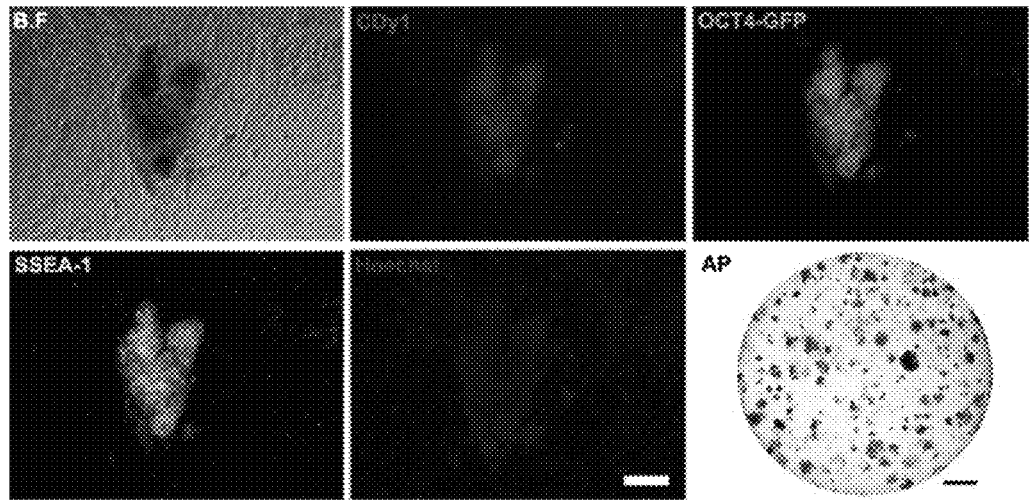
FIG. 8 shows images of iPSC characterization and staining with CDy1. GFP-expressing iPSC colonies generated from Oct4-GFP transgenic mouse MEF were further characterized by alkaline phosphatase assay ("AP") and SSEA-1 immunostaining. These images show that the CDy1 signal overlaps with the GFP signal and SSEA-1 staining (Scale bar, 200 µm for fluorescence image; 500 µm for AP).
Figure 9:
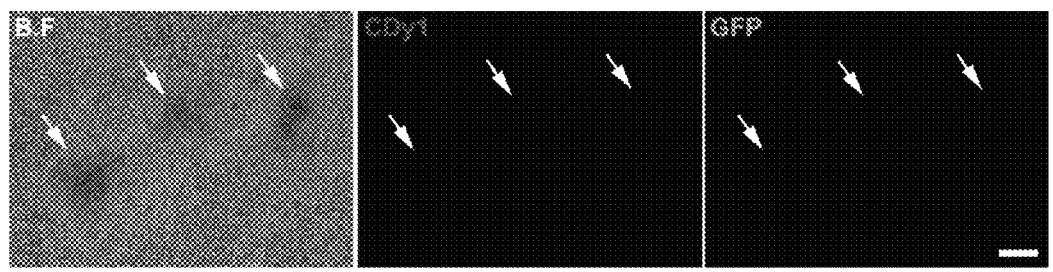
FIG. 9 shows images of CDy1-negative, GFP-negative cell colonies. Some colonies generated during the iPSC induction procedure were not stained by CDy1. Without fluorescence, those colonies would have been morphologically indistinguishable from the others (Scale bar, 100 µm).

Having found that CDy1 selectively stains ESC, the dye was applied to iPSCs generated from MEF of transgenic mice that express GFP under the control of the Oct4 (also known as Pou5f1) promoter. The reprogramming was performed in a 6-well culture dish by retroviral introduction of four transcriptions factors: Oct4, Sox2, Klf4, and c-Myc (Takahashi et al., "Induction of Pluripotent Stem Cells from Mouse Embryonic and Adult Fibroblast Cultures by Defined Factors," *Cell*, 126(4):663-676 (2006), which is hereby incorporated by reference in its entirety). iPSC generation was verified by GFP expression, alkaline phosphatase assay, and immunostaining of SSEA-1 at 17 days post infection ("dpi"). It was found that CDy1 also selectively stained the iPSC colony (FIG. 8). When the 155 colonies grown in 6-well plate cells were treated with CDy1 at 17 dpi, 101 colonies (65%) were both CDy1 and GFP positive, 26 (17%) were CDy1-only positive, 4 (3%) were GFP-only positive and 24 (15%) were negative both for CDy1 and GFP, despite the fact that the morphology of the colonies was indistinguishable (FIG. 9).

Figure 10A:
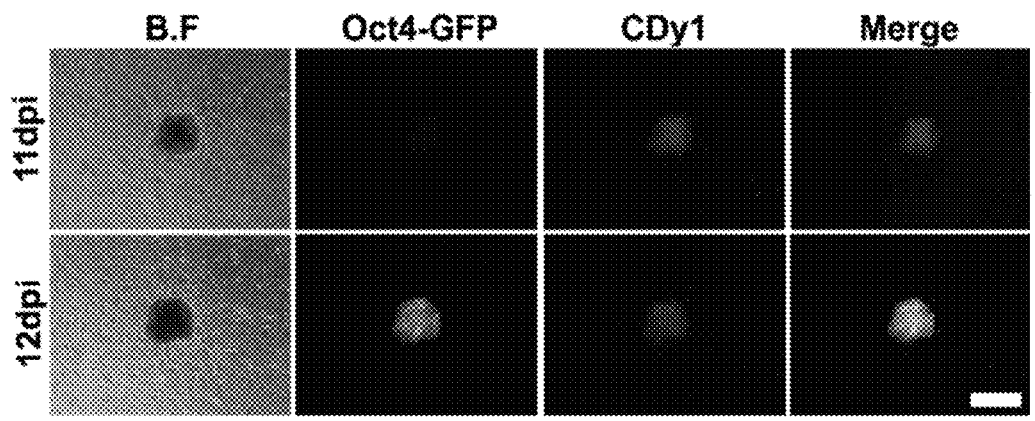
FIGS. 10A-10C show results of iPSC staining by CDy1 at an early stage of reprogramming
Figure 10B:
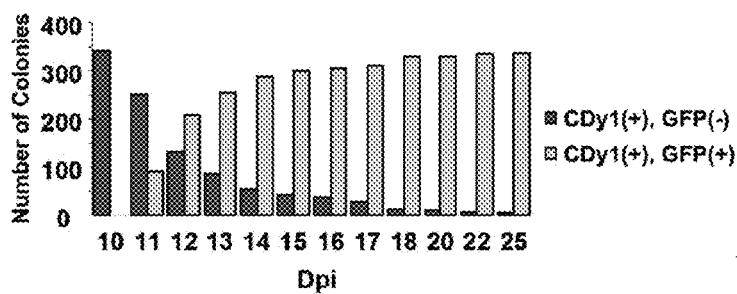
Figure 10C:
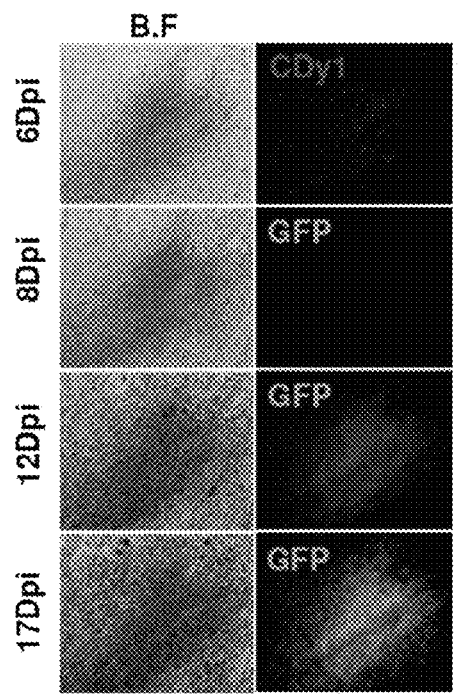

In a cell culture treated with CDy1 at an earlier time point of iPSC generation (10 dpi), increasing numbers of CDy1-stained colonies started to show GFP signal during the following days (FIG. 10A). To perform a more systematic analysis, the cells were stained with CDy1 at 2 dpi (i.e., when iPSC was not distinguishable by any means) and the CDy1 and GFP signals were tracked by daily acquisition of cell images using an ImageXpress$^{MICRO}$ system. At 10 dpi, when small colonies started to appear, 342 CDy1-positive but GFP-negative colonies were selected and their GFP expression was followed until 25 dpi. An increasing number of colonies started to express GFP during this period, and 338 (99%) out of the 342 tracked colonies were GFP-positive at 25 dpi (FIG. 10B). During this period, no detectable differences in the number of GFP-positive colonies or cell morphology were observed compared to untreated iPSC. In addition, as shown in FIG. 10C, the cells that expressed GFP at 12 dpi were stained by CDy1 as early as 6 dpi.

Figure 11:
FIG. 11 shows results of differentiated mESC staining with CDy1. Morphologically distinguishable differentiated cells were observed after three days culture of mESC in the absence of LIF. As shown in the center panel, most of those cells were CDy1 negative, while some other cells that retained mESC morphology were stained by the dye. As shown by the right panel, immunocytochemistry with Oct4 antibody performed on the following day showed a similar pattern of staining with CDy1 (B.F, bright field; scale bar, 100 µm).

On the other hand, removing the LIF from the culture media induced mESC differentiation and it was observed that some cells were morphologically distinguishable from mESC three days later. Most of the differentiated cells were not stained by CDy1, while some other cells with mESC morphology were stained by the dye showing a similar pattern with immunocytochemical staining by Oct4 antibody (FIG. 11). This result was further confirmed in lineage specific cells differentiated from mESC via embryoid body formation (FIG. 7).

Example 4

CDy1 Localizes to Mitochondria in Embryonic Stem Cells

Figure 12:
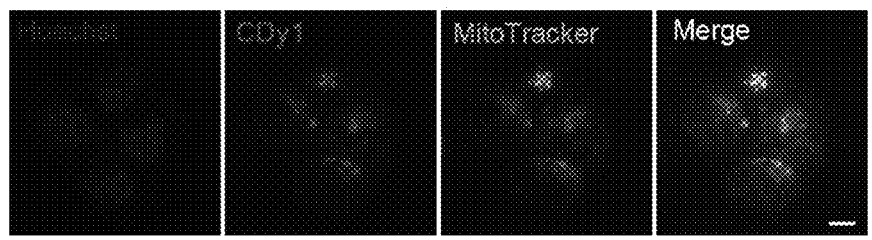
FIG. 12 shows co-localization of CDy1 and MITOTRACKER®. In this experiment mESC were incubated with 500 nM CDy1, 200 nM MITOTRACKER® Deep Red 633, and 4 mg/ml Hoechst for 30 minutes at 37° C. and washed with PBS two times. The cells were mounted on slide glass and the images were taken using a Nikon ECLIPSE Ti fluorescence microscope equipped with a ×100 objective lens (Pearson's correlation coefficient=0.88; scale bar, 5 µm).

In a previous study (Kim et al., "Control of Muscle Differentiation by a Mitochondria-Targeted Fluorophore," *J. Am. Chem. Soc.* 132(2): 576-579 (2009), which is hereby incorporated by reference in its entirety), CDy1 was among the compounds targeting mitochondria. To examine whether CDy1 localizes in mitochondria in mESC, the cells were co-stained with CDy1 and a mitochondria-staining commercial dye MITOTRACKER® Deep Red 633. It was observed that the CDy1 staining pattern was very similar to MITOTRACKER® staining (FIG. 12). In addition to the mitochondrial membrane potential which sequesters many cationic rhodamine and rosamine compounds, other factors such as stem cell specific proteins appear to play roles in the entry and retainment of CDy1 rendering it stem cell selective.

Example 5

Comparison of CDy1 with ALDEFLUOR® Staining

Figure 13:
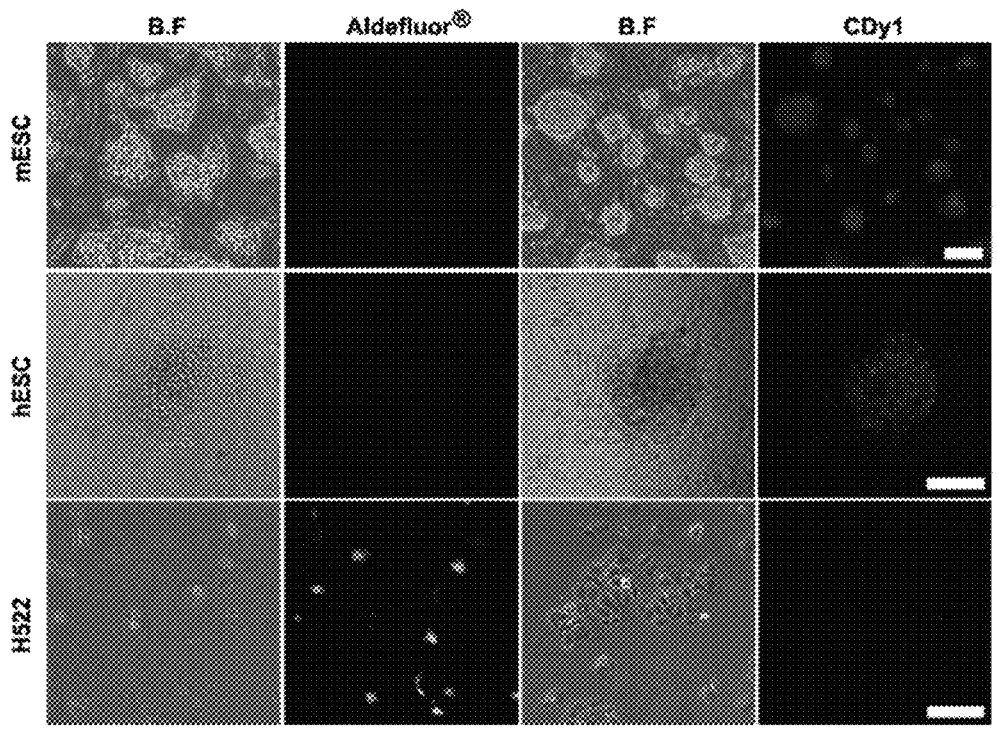
FIG. 13 shows a comparison of CDy1 and ALDEFLUOR® staining in mESC and human ESC (hESC) (BG01V). As shown, ALDEFLUOR® does not stain ESC, whereas CDy1 stains ESC but not a H522 human lung cancer cell line which expresses ALDH1a1 (normally stained by ALDEFLUOR®). In this experiment, the cells cultured on 6-well plates were incubated with 1 µM ALDEFLUOR® for one hour at 37° C. and then washed with PBS three times before ALDEFLUOR® assay buffer was added. Bright field ("B.F") and fluorescence (FITC filter for ALDEFLUOR® and TRITC filter for CDy1) images were taken using a Nikon ECLIPSE Ti fluorescence microscope (Scale bars, 100 µm).
Figure 14:
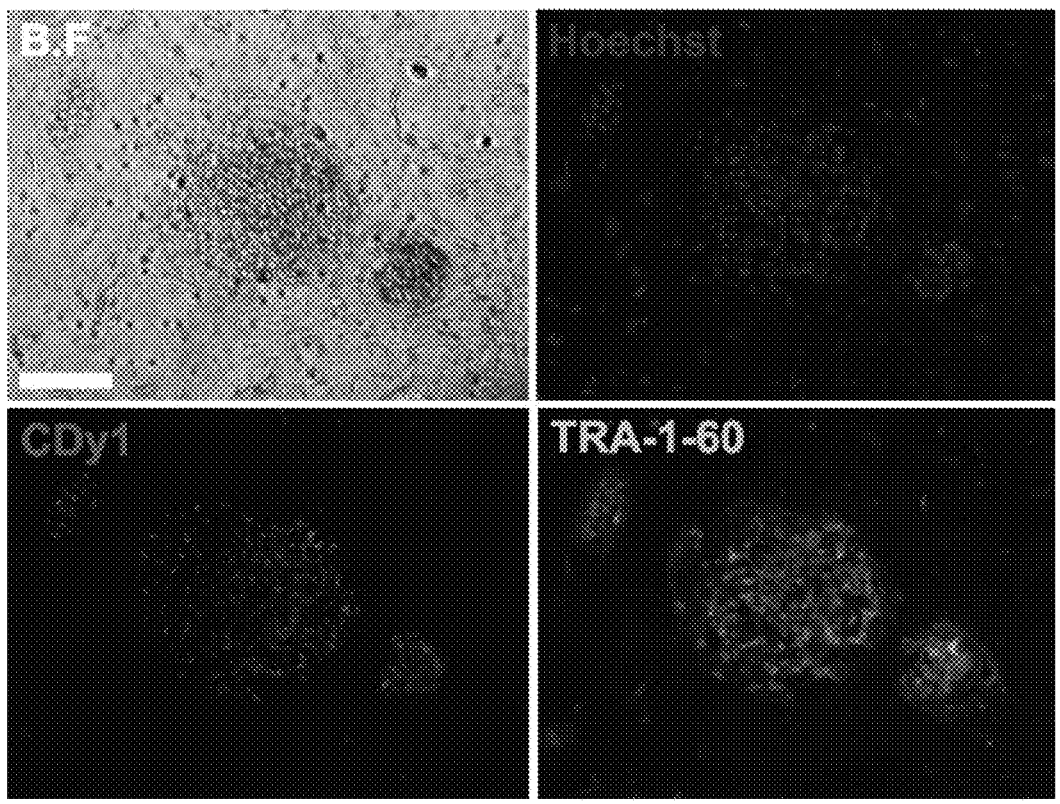
FIG. 14 shows hESC BG01V characterization and staining with CDy1. BG01V cells cultured on MEF were selectively stained by CDy1. The expression of hESC marker TRA-1-60 in the CDy1-stained BG01V cells was detected by immunofluorescence staining (Scale bar, 100 µm).

Among the few fluorescent dyes used for stem cell staining (Zijlmans et al., "Modification of Rhodamine Staining Allows Identification of Hematopoietic Stem Cells with Preferential Short-term or Long-term Bone Marrow-Repopulating Ability," Proc. Natl. Acad. Sci. USA, 92:8901-8905 (1995), which is hereby incorporated by reference in its entirety) is ALDEFLUOR® which employs a fluorescent substrate BODIPY-aminoacetaldehyde for aldehyde dehydrogenase (ALDH)1A1 (Storms et al., "Isolation of Primitive Human Hematopoietic Progenitors on the Basis of Aldehyde Dehydrogenase Activity," Proc. Natl. Acad. Sci. USA, 96: 9118-9123 (1999), which is hereby incorporated by reference in its entirety). It has been used to identify and isolate certain types of stem cells including hematopoietic, neural, and mammary stem cells as well as cancer stem cells. Whether or not ALDEFLUOR® stains ESC has not been known. Accordingly, the cell selectivity of CDy1 was compared with ALDEFLUOR® and it was observed that ALDEFLUOR® stains neither mESC nor human ESC (hESC). Reciprocally, CDy1 stained both mESC and hESC but not a human lung cancer cell line H522 which is known to express a high level of ALDH1A1 and be stained by ALDEFLUOR® (Moreb et al., "Heterogeneity of Aldehyde Dehydrogenase Expression in Lung Cancer Cell Lines is Revealed by Aldefluor Flow Cytometry-based Assay," Cytometry B Clin. Cytom., 72: 281-289 (2007), which is hereby incorporated by reference in its entirety) (FIG. 13). The stemness of hESC BG01V used in this study was verified by immunocytochemical staining of TRA-1-60 (FIG. 14).

Example 6

Isolation of Cells Undergoing Reprogramming into Induced Pluripotent Stem Cells at Early Stages Using CDy1

Oct4-GFP transgenic mouse embryonic fibroblasts (MEF) transfected with retrovirus expressing Oct4, Sox2, Klf4, and c-Myc were incubated with CDy1 at 10 days post infection (dpi). The cells were harvested using trypsin-EDTA and CDy1$^{bright}$ and CDy1$^{dim}$ cells defined as 7% of the total cell number at each end were collected by FACS, plated in culture media, and allowed to grow until 20 dpi for counting the number of induced pluripotent stem ("iPS") cell colonies which were identified by GFP signal (FIG. 15A).

Figure 15:
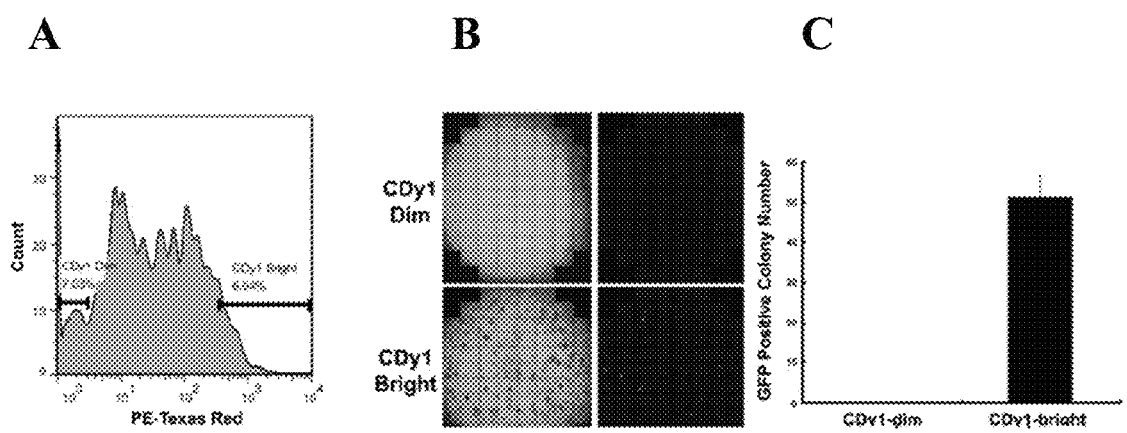
FIGS. 15A-C demonstrate selective staining of cells undergoing reprogramming into induced pluripotent stem cells using CDy1.

Among the many cell colonies observed in the bright field images, GFP signal was detected from some of them by fluorescence excitation (FIG. 15B). The CDy1$^{bright}$ cells generated 51 GFP-positive iPS cell colonies per well but no colonies were observed in CDy1$^{dim}$ cell plated well (FIG. 15C). This result shows that live cells undergoing reprogramming can be isolated using CDy1.

Example 7

Identification of CDy1 Positive Cells at Early Stages of Reprogramming into Induced Pluripotent Stem Cells Oct4-GFP transgenic MEF transfected with retrovirus expressing Oct4, Sox2, Klf4, and c-Myc were incubated with CDy1 at 3, 5, 7, and 9 dpi for one hour.

After excess CDy1 was washed out by replacing culture medium, fluorescent cell images were taken using fluorescence microscope.

Figure 16:
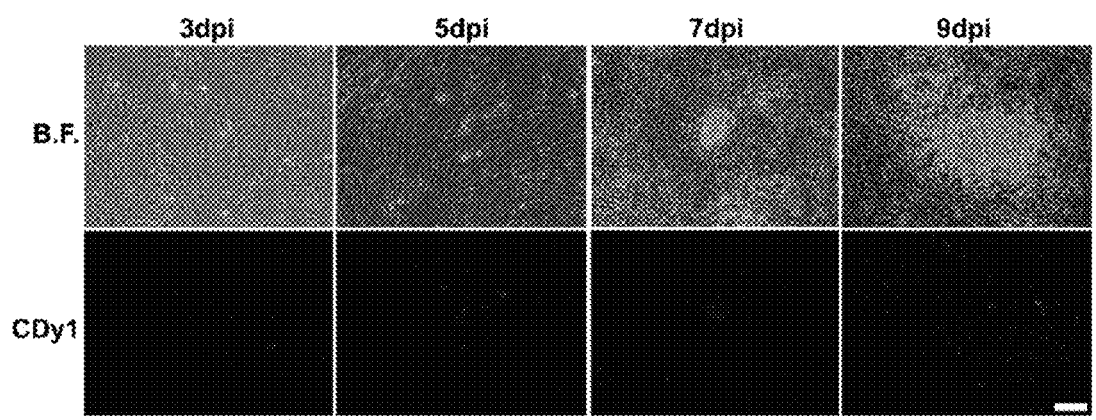
FIG. 16 shows fluorescent cell images of Oct4-GFP transgenic MEF transfected with retrovirus expressing Oct4, Sox2, Klf4, and c-Myc and incubated with CDy1 at 3, 5, 7 and 9 dpi. At 3 and 5 dpi, any dramatic morphological differences between the cells were not observed by phase contrast bright field microscopy. However, fluorescence microscopy identified scattered single cells stained by CDy1. At 7 and 9 dpi cell clusters started to be observed by phase contrast bright field microscopy and some of the clusters were stained by CDy1.

At 3 and 5 dpi, any dramatic morphological differences between the cells were not observed by phase contrast bright field microscopy (FIG. 16). However, fluorescence microscopy identified scattered single cells stained by CDy1. At 7 and 9 dpi cell clusters started to be observed by phase contrast bright field microscopy and some of the clusters were stained by CDy1 (FIG. 16). This result shows that the cells undergoing reprogramming can be identified by CDy1 at very early stages even before morphological changes are observed.

Example 8

Global Gene Expression Analysis of Cells Isolated Using CDy1 at Early Stages of Reprogramming Oct4-GFP transgenic MEF transfected with retrovirus expressing Oct4, Sox2, Klf4, and c-Myc were incubated with CDy1 every 2nd day from 3 dpi to isolate CDy1$^{bright}$ cells at 3, 5, 7, and 9 dpi by FACS before the activation of endogenous Oct4 promoter determined by GFP expression. Global gene expression profiles of CDy1$^{bright}$ cells were analyzed by DNA microarray. RNAs extracted from MEF, CDy1$^{bright}$ cells at 15 dpi, a mature iPS cell line (S3-C-2) of passage 7, and mouse embryonic stem cells (mESC) were also included for the analysis. For the microarray, purified and labeled cRNA was hybridized onto MouseRef-8 v2 expression BeadChips (Illumina, San Diego, Calif.). Each sample was run in duplicate. The bead intensities were mapped to gene information using BeadStudio 3.2 (Illumina, San Diego, Calif.). The data were exported as text file for quantile normalization, variance stabilization using log 2 scaling, differentially expressed gene (DEG) finding, and hierarchical clustering using GenPlex software package (Istech, Goyang City, Korea).

Figures 17A, 17B:
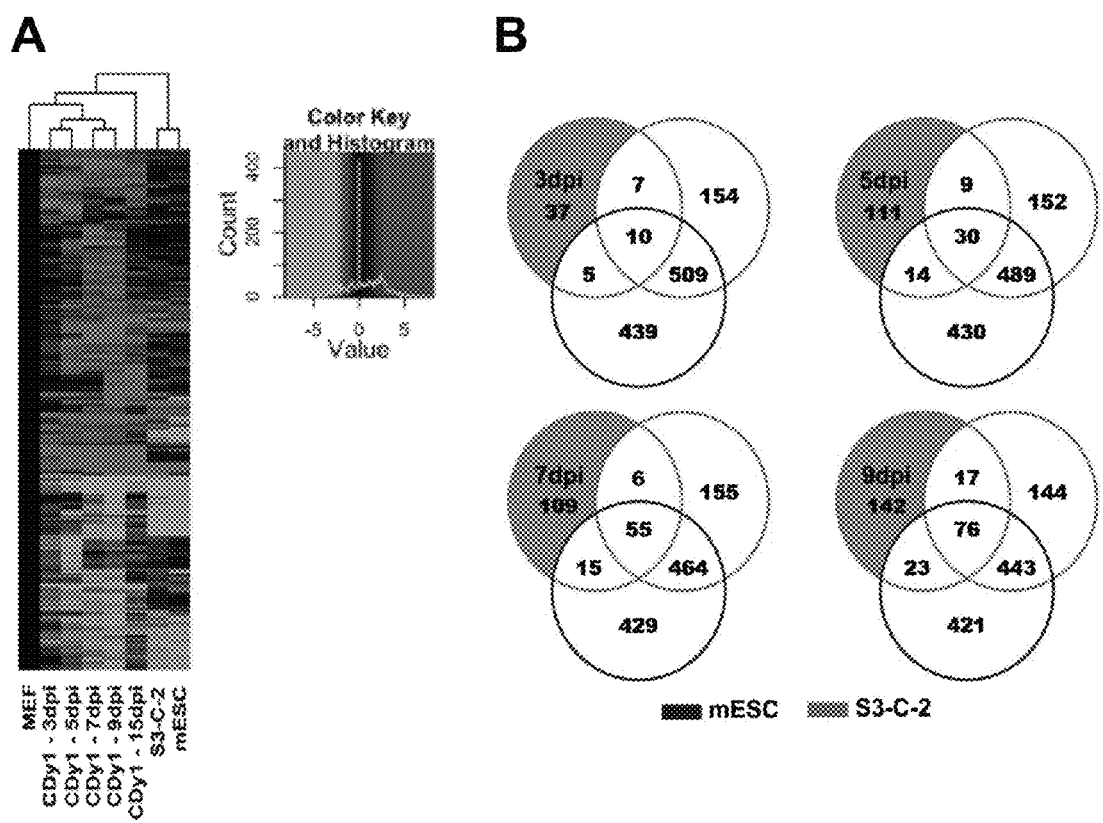
FIG. 17A shows a heat map generated from the genes differentially expressed ("DEG") more than 5-fold at 3, 5, 7, and 9 dpi. It illustrates a distinct difference between the cells at early stages of reprogramming and mature induced pluripotent cells (which are similar to embryonic stem cells).
FIG. 17B shows Venn diagrams illustrating that among 5-fold DEG, 37 (3 dpi), 111 (5 dpi), 109 (7 dpi), and 142 (9 dpi) genes were exclusively for early time points which were not identified in a mature induced pluripotent stem cell line (S3-C-2) or an embryonic stem cell line (mESC).

With 5-fold difference criteria, 59 (3 dpi), 164 (5 dpi), 185 (7 dpi), and 258 (9 dpi) DEG were identified. The heat map generated from the DEG shows a distinct difference between the cells at early stages of reprogramming and mature iPS cells (which are similar to ES cells) (FIG. 17A). Among the 5-fold DEG, 37 (3 dpi), 111 (5 dpi), 109 (7 dpi), and 142 (9 dpi) genes were exclusively for early time points which were not identified in a mature iPS cell line (S3-C-2) or ES cell line (mESC) (FIG. 17B).

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of detecting, in a sample, one or more embryonic stem cells or induced pluripotent stem cells, said method comprising:
   providing a sample potentially containing one or more embryonic stem cells or induced pluripotent stem cells;
   providing a rosamine derivative compound of the formula:

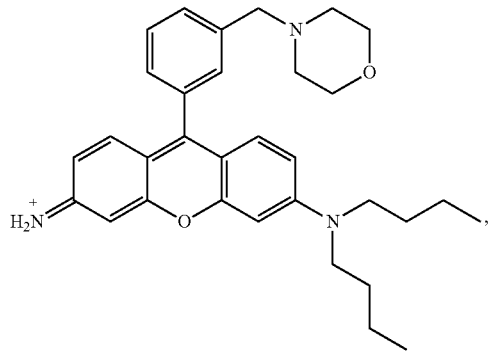 [SMILES: CCCCN(CCCC)c1ccc2c(-c3cccc(CN4CCOCC4)c3)c3ccc(=N)cc-3oc2c1]

wherein the rosamine derivative compound selectively produces fluorescent signals when contacted with embryonic stem cells or induced pluripotent stem cells;
   contacting the sample with the rosamine derivative compound; and
   detecting the presence of one or more embryonic stem cells or induced pluripotent stem cells based on fluorescent signals emitted by the sample following said contacting.

2. The method according to claim 1, further comprising detecting differentiated cells by fluorescent signals that are different than the fluorescent signals emitted by the embryonic stem cells or induced pluripotent stem cells.

3. The method according to claim 1, wherein said method is utilized to detect embryonic stem cells in a sample having a mixed cell population.

4. The method according to claim 1, wherein said method is utilized to detect induced pluripotent stem cells in a sample having a mixed cell population.

5. The method according to claim 1, wherein the rosamine derivative compound targets mitochondria in the embryonic stem cells.

6. The method according to claim 1 further comprising:
isolating the one or more embryonic stem cells or induced pluripotent stem cells from the sample.

7. A method of detecting, in a sample, one or more cells undergoing reprogramming to produce induced pluripotent stem cells, said method comprising:
providing a sample potentially containing one or more cells undergoing reprogramming to produce induced pluripotent stem cells;
providing a rosamine derivative compound of the formula:

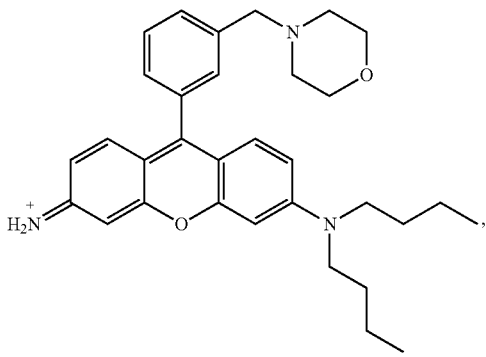 [SMILES: CCCCN(CCCC)c1ccc2c(-c3cccc(CN4CCOCC4)c3)c3ccc(=N)cc-3oc2c1]

wherein the rosamine derivative compound selectively produces fluorescent signals when contacted with cells undergoing reprogramming to produce induced pluripotent stem cells;

contacting the sample with the rosamine derivative compound; and detecting the presence of the one or more cells undergoing reprogramming to produce induced pluripotent stem cells based on fluorescent signals emitted by the sample following said contacting.

8. The method according to claim 7 further comprising:
isolating the one or more cells undergoing reprogramming to produce induced pluripotent stem cells from the sample.

9. The method according to claim 1, wherein said one or more cells undergoing reprogramming comprise one or more cells that are Oct4 negative.

* * * * *

SEQUENCE LISTING

<160> NUMBER OF SEQ ID NOS: 4

<210> SEQ ID NO 1
<211> LENGTH: 24
<212> TYPE: DNA
<213> ORGANISM: Artificial
<220> FEATURE:
<223> OTHER INFORMATION: Nanog sense primer

<400> SEQUENCE: 1
agggtctgct actgagatgc tctg                                          24

<210> SEQ ID NO 2
<211> LENGTH: 24
<212> TYPE: DNA
<213> ORGANISM: Artificial
<220> FEATURE:
<223> OTHER INFORMATION: Nanog antisense primer

<400> SEQUENCE: 2
caaccactgg tttttctgcc accg                                          24

<210> SEQ ID NO 3
<211> LENGTH: 20
<212> TYPE: DNA
<213> ORGANISM: Artificial
<220> FEATURE:
<223> OTHER INFORMATION: GAPDH sense primer

<400> SEQUENCE: 3
gcacagtcaa ggccgagaat                                               20

<210> SEQ ID NO 4
<211> LENGTH: 20
<212> TYPE: DNA
<213> ORGANISM: Artificial
<220> FEATURE:
<223> OTHER INFORMATION: GAPDH antisense primer

<400> SEQUENCE: 4
gccttctcca tggtggtgaa                                               20